(12) United States Patent
Lapidot et al.

(10) Patent No.: US 8,241,903 B2
(45) Date of Patent: Aug. 14, 2012

(54) CATECHOLAMINE RECEPTOR MODULATION

(75) Inventors: Tsvee Lapidot, Ness Ziona (IL); Asaf Spiegel, Ganei Tikva (IL); Menachem Rubinstein, Rehovot (IL); Alexander Kalinkovich, Rehovot (IL); Shoham Shivtiel, Moshav Kahal (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 663 days.

(21) Appl. No.: 12/306,030

(22) PCT Filed: Jun. 19, 2007

(86) PCT No.: PCT/IL2007/000741
§ 371 (c)(1),
(2), (4) Date: Dec. 22, 2008

(87) PCT Pub. No.: WO2007/148332
PCT Pub. Date: Dec. 27, 2007

(65) Prior Publication Data
US 2009/0191162 A1    Jul. 30, 2009

(30) Foreign Application Priority Data

Jun. 22, 2006 (IL) .......... 176507
Dec. 5, 2006 (IL) .......... 179849

(51) Int. Cl.
*C12N 5/074* (2010.01)
*C12N 5/078* (2010.01)
*C12N 5/0789* (2010.01)

(52) U.S. Cl. .......... 435/372; 424/93.1; 514/7.9

(58) Field of Classification Search .......... None
See application file for complete search history.

(56) References Cited

U.S. PATENT DOCUMENTS

2002/0192817 A1 * 12/2002 Weiss et al. .......... 435/368
2009/0010873 A1 * 1/2009 Eisenbach-Schwartz et al. .......... 424/85.2

FOREIGN PATENT DOCUMENTS

WO   WO 2004/103262   12/2004

OTHER PUBLICATIONS

Katayama, Y. et al. "Signals from the Sympathetic Nervous System Regulate Hematopoietic Stem Cell Egress from Bone Marrow" *Cell*, Jan. 27, 2006, pp. 407-421, vol. 124, XP-002456454.

Liu, W. et al. "Neuroprotection by Pergolide Against Levodopa-Induced Xytotoxicity of Neural Stem Cells" *Neurochemical Research*, Dec. 2004, pp. 2207-2214, vol. 29, No. 12.

Nishimura, F. et al. "Potential Use of Embryonic Stem Cells for the Treatment of Mouse Parkinsonian Models: Improved Behavior by Transplantation of In Vitro Differentiated Dopaminergic Neurons from Embryonic Stem Cells" *Stem Cells*, 2003, pp. 171-180, vol. 21, XP-002456455.

* cited by examiner

*Primary Examiner* — Daniel C Gamett
(74) *Attorney, Agent, or Firm* — Saliwanchik, Lloyd & Eisenschenk

(57) ABSTRACT

The invention relates to receptors of catecholamines and their role in stem cell development and function.

20 Claims, 10 Drawing Sheets

CATECHOLAMINE RECEPTOR MODULATION

This application is the U.S. national stage application of International Patent Application No. PCT/IL2007/000741, filed Jun. 19, 2007, the disclosure of which is hereby incorporated by reference in its entirety, including all figures, tables and amino acid or nucleic acid sequences.

FIELD OF THE INVENTION

The invention relates to receptors of catecholamines and their role in stem cell development and function.

BACKGROUND OF THE INVENTION

Bone marrow transplantation (BMT) or hematopoietic stem cell transplantation (HSCT) is a medical procedure in the field of hematology and oncology that involves transplantation of hematopoietic stem cells (HSC). BMT and HSCT are most often employed in the treatment of patients suffering of diseases of the blood or bone marrow, or certain types of cancer. The objective of BMT or HSCT transplantation is to provide the patient with a healthy stem cell population that will differentiate into mature blood cells that replace deficient or pathologic cell lineages.

Hematopoietic stem cells are a rare population of cells within the bone marrow microenvironment. Hematopoietic stem cells actively maintain the continuous production of all mature blood cell lineages, which include major components of the immune system such as T and B Lymphocytes throughout life while maintaining a small pool of undifferentiated stem and progenitor cells (Mayani, 2003).

In the case of a bone marrow transplant (BMT), the HSC are removed from a large bone of the donor, typically the pelvis, through a large needle that reaches the center of the bone. The technique is referred as a bone marrow harvest and is performed with general anesthesia because literally hundreds of insertions of the needle are required to obtain sufficient material.

Peripheral blood stem cells (PBSC) are now the most common source of stem cells for HSCT. PBSC are collected from the blood through a process known as apheresis. The peripheral stem cell yield is boosted with daily subcutaneous injections of granulocyte colony-stimulating factor (G-CSF).

Another source of stem cells is umbilical cord blood. Cord blood has a higher concentration of HSC than is normally found in adult blood. However, the small quantity of blood that can be obtained from an umbilical cord (typically about 50 ml) makes this source less suitable for transplantation into adults. Newer techniques using ex-vivo expansion of cord blood units or the use of 2 cord blood units from different donors are being explored to facilitate cord blood transplants in adults.

During development, or in experimental and clinical transplantation, stem cells migrate through the blood circulation and home into the bone marrow (BM), repopulating it with immature and maturing myeloid and lymphoid blood cells, which in turn are released into the circulation. The process of hematopoietic stem cell homing and repopulation, which is crucial for stem cell function and development of the immune system, is not well understood.

In order to study the processes of hematopoietic stem cell homing and repopulation, several groups have established in vivo models including engraftment (incorporation of grafted tissue or cells into the body of the host) of human stem cells into immune deficient mice such as irradiated beige, nude, Xid (X-linked immune deficiency), SCID and non-obese diabetic SCID (NOD/SCID) mice, and in utero transplantation into sheep fetuses, which resulted in successful multilineage engraftment of both myeloid and lymphoid cells (McCune et al., 1988; Nolta et al., 1994; Lapidot et al., 1992; Larochelle et al., 1996; Civin et al., 1996).

The present inventors have developed a functional in vivo assay for primitive human SCID repopulating cell (SRCs) based on their ability to durably repopulate the bone marrow of intravenously transplanted SCID or NOD/SCID mice with high levels of both myeloid and lymphoid cells (Lapidot et al., 1992; Larochelle et al., 1996). Kinetic experiments demonstrated that only a small fraction of the transplanted cells engrafted and that these cells repopulated the murine bone marrow by extensive proliferation and differentiation. Furthermore, the primitive human cells also retained the capacity to engraft secondary murine recipients (Cashman et al., 1997). Transplantation of populations enriched for CD34 and CD38 cell surface antigen expression, revealed that the phenotype of SRC is $CD34^+CD38^-$ (Larochelle et al., 1996). Other repopulating cells may exist since other studies suggest that immature human $CD34^-$ cells and more differentiated $CD34^+ CD38^+$ cells have some limited engraftment potential (Zanjani et al., 1998; Conneally et al., 1997).

Homing of human stem cells and their subsequent proliferation and differentiation in transplanted immune deficient mice was found to be dependent on interactions between chemokine stromal derived factor one (SDF-1), which is expressed by the host bone marrow, and its receptor CXCR4, which is expressed on the donor homing cells. Interfering with SDF-1/CXCR4 interactions by pretreatment of immature human $CD34^+$ cells with neutralizing anti CXCR4 antibody blocked their in vivo homing and repopulation, while untreated cells could home within hours into the BM of recipient mice [Peled et al., 1999 (a)].

Increasing CXCR4 expression on the cell surface of stem cells, by cytokine stimulation, was found to enhance the response to SDF-1 of these cells manifested by improvement of homing and engraftment. Immature human $CD34^+$ cells that do not express cell surface CXCR4 contain internal CXCR4, which can oscillate in vivo following transplantation. Prevention of this CXCR4 cell surface up regulation blocked the low levels of human $CD34^+$ $CXCR4^-$ cell engraftment. Thus, the phenotype of repopulating human stem cells was defined as $CD34^+ CD38^{-/low}CXCR4+$ cells (Kollet et al., 2002).

SDF-1 (also named CXCL12) is produced by many cell types including bone marrow stromal and endothelial cells, and as mentioned, is a powerful chemoattractant for immature and mature hematopoietic cells, and regulates leukocyte trafficking in steady state homeostasis. SDF-1 serves as a survival factor for stem and progenitor cells, and is involved in immature B cell and megakaryocyte development (McGrath et al., 1999; Nagasawa et al., 1996). SDF-1 is highly preserved throughout evolution. For example, human and mouse SDF-1 are cross-reactive and differ only in one amino acid.

Release and mobilization of stem cells from the bone marrow into the circulation are induced for clinical transplantation. Multiple stimulations with cytokines such as G-CSF are used to recruit human stem cells from the circulation. SDF-1/CXCR4 interaction within the BM following G-CSF administration was found to be involved in the mobilization process (Petit et al., 2002).

Proteolytic enzymes such as neutrophil elastase were found to degrade SDF-1 in the bone marrow during G-CSF administration. In parallel, the levels of CXCR4 expression on hematopoietic cells within the bone marrow were found to increase prior to their mobilization. Neutralizing antibody for CXCR4 or SDF-1 reduced human and mouse stem cell mobilization, demonstrating SDF-1/CXCR4 signaling in cell egress (Petit et al., 2002).

Thus, stem cell homing and release/mobilization utilize similar mechanisms, and in both processes SDF-1/CXCR4 interactions play a major role.

SDF-1 also plays an important role in the migration of leukemic cells. While normal and leukemic cells share similar mechanisms of migration, different homing patterns as well as SDF-1 signaling pathways were found when comparing malignant human Pre-B ALL cells (B-cell precursor acute lymphoblastic leukemia) to normal immature $CD34^+$ cells (Spiegel et al., 2004). In acute myelogenous leukemia (AML), another malignant disease, high levels of intracellular CXCR4 and SDF-1 have been found in all leukemic cells, including cells that do not express surface CXCR4. CXCR4 is essential for the homing of these cells to the BM of immune deficient mice, demonstrating dynamic regulation of CXCR4 in these cells. (Tavor et al., 2005).

The expression of SDF-1 on the cell surface of endothelial cells within the blood vessels was found to be crucial for inducing cell arrest under shear flow, an essential step for a successful transendothelial migration from the circulation into the bone marrow. In addition, SDF-1 activated the major adhesion molecules such as CD44, LFA-1, VLA-4 and VLA-5 on migrating human stem and progenitor cells as part of the multistep process of homing and transendothelial migration (Peled et al., 2000). It has been suggested that SDF-1 mediates adhesion and anchorage of stem cells to the extracellular matrix of the BM niches by altering the cytoskeleton and relocating surface CD44 expression (Avigdor et al., 2004).

The mechanisms that induce cell motility and migration following SDF-1 stimulation and signal transduction pathways, which are triggered by binding of SDF-1 to CXCR4, are not known. Activation of PI3K, but not MAPK, has been found to be required for motility of enriched immature $CD34^+$ cells. The atypical PKC zeta isoform was found to be essential for the process of migration. Moreover, activation of PKC zeta by SDF-1 was found to be PI3K dependent (Petit et al., 2005).

Beside its role in migration and adhesion, SDF-1 is also involved in proliferation and survival of various cells including normal human $CD34^+$ cells and leukemic cells (Lee et al., 2002; Nishii et al. 1999, and Tavor et al., 2005).

Catecholamines are derived from the amino acid tyrosine. Catecholamines have a benzene ring with two hydroxyl groups, an intermediate ethyl chain and a terminal amine group (Lehninger, Principles of Biochemistry).

Catecholamines such as epinephrine (adrenaline), norepinephrine (noradrenaline) and dopamine may be regarded as derivatives of catechol or 1,2-dihydroxybenzene and they function as neurotransmitter substances (Lehninger, Principles of Biochemistry).

High epinephrine levels in blood are associated with stress, which can be induced from psychological reactions or environmental stressors. Epinephrine causes general physiological changes such as increases in heart rate, blood pressure, and blood glucose levels (Lehninger, Principles of Biochemistry).

Some drugs, like tolcapone (a central COMT-inhibitor), raise the levels of all the catecholamines (Wikipedia).

The adrenergic receptors (or adrenoceptors) are a class of G protein-coupled receptors that are targets of the catecholamines. Adrenergic receptors specifically bind their endogenous ligands, the catecholamines adrenaline and noradrenaline, and are activated by these (Wikipedia).

α-adrenergic receptors bind norepinephrine and epinephrine, though norepinephrine has higher affinity. Phenylephrine is a selective agonist of the a receptor (Wikipedia).

Dopamine is one of the three major catecholamine neurotransmitters in a variety of organs. Dopamine receptors have been widely established as key regulators of cardiovascular, renal, hormonal, central nervous system and ocular functions. In the brain, dysfunction of the dopaminergic system leads to Parkinson's disease and schizophrenia (Lim et al. 2005, Foley et al. 2004, and Goldman et al. 2004). Dopamine receptor subtypes belong to the family of G-protein-coupled receptors and share the characteristic structure of seven transmembrane domains. Five dopamine receptor subtypes can be classified into two families, referring to analogies in sequence and in signal transduction. The D1-like dopamine receptors include the dopamine D1 and the D5 receptors. They are characterized by activation of adenylyl cyclase mediated by a Gs protein, consequently effecting higher concentrations of the secondary messenger cyclic adenosine-3, 5-monophosphate (cAMP). The genes of the D1-like dopamine receptors lack introns. The D2-like receptor group consists of the dopamine D2, D3, and D4 receptors, which couple to Gi/0 proteins and can inhibit adenylyl cyclase. In the genes of dopamine D2-like receptors introns can be found (Sibley et al. 1992).

A role of different 7-transmembrane receptors, neurokinin-1 and 2, in hematopoiesis was recently reported. This study discloses that p53 partly regulates the anti proliferative effect of one of the ligands of NK2 receptor, the neurotransmitter neurokinin-A, on progenitor cells. This effect could be reversed by the cytokine GM-CSF (Vishalakumar et al. 2005).

A crosstalk between the immune system and the neuronal system was previously suggested, and neuro-immune interactions enable mutual regulation of the nervous and immune systems. Reports indicate that dopamine is one of the important mediators of neuro-immune interactions (Basu et al. 2000). Ilani et al (2004) suggested a pathway by which the brain affects and regulates immune activated T cells. Levite et al (2001) and Besser (2005) showed that dopamine could directly activate T cells via its specific receptors and suggest a possible role for dopamine in integrin-mediated trafficking and extravasation of T cells in the central nervous system and possibly in the periphery.

SUMMARY OF THE INVENTION

In one aspect, the invention relates to the use of a catecholamine receptor agonist, optionally in combination with an agent capable of up-regulating the expression level of the catecholamine receptor in stem cells or progenitors, in the manufacture of a medicament for improving or facilitating stem cell transplantation (SCT) and/or progenitor transplantation therapy.

In one embodiment of the invention, the medicament is for improving or facilitating hematopoietic stem cell transplantation (HSCT) and/or hematopoietic progenitor transplantation.

In a further embodiment of the invention, the medicament is for improving or facilitating repopulation of mature blood cell lineages.

In a further embodiment of the invention the medicament is for administration ex-vivo to the stem cells and/or progenitor cells before transplantation, thereby increasing, migration, engraftment capacity and/or proliferation of the stem cells and/or progenitor cells.

In a further embodiment of the invention the stem cells and/or progenitors used for transplantation are from a G-CSF treated donor.

In a further embodiment of the invention the medicament comprises an agent capable of up-regulating the expression level of the catecholamine receptor in stem cells or progenitors, such as a myeloid cytokine like GM-CSF and/or G-CSF or an expression vector encoding the catecholamine receptor.

In another embodiment of the invention, the medicament is for administration in vivo to a healthy donor or to a patient undergoing cancer therapy, thereby increasing mobilization of stem cells or progenitors from the bone marrow and other tissues sites into the blood and facilitating stem cells and/or progenitors collection from the blood for transplantation.

The invention provides the use of a catecholamine receptor agonist, optionally in combination with a myeloid cytokine, in the manufacture of a medicament for improving or facilitating mobilization of stem cells and/or progenitors from the bone marrow and other tissue sites into the blood and facilitating stem cells and/or progenitors collection from the blood of a healthy donor or of a patient undergoing cancer therapy.

In addition, the invention provides the use of catecholamine receptor agonist in combination with a myeloid cytokine, in the manufacture of a medicament for improving or facilitating hematopoietic stem cell transplantation (HSCT) and/or hematopoietic progenitor cell transplantation therapy for repopulation of mature blood cell lineages, wherein the medicament is for administration to the stem cells and/or progenitor cells ex-vivo before transplantation, thereby increasing engraftment capacity and/or proliferation of the stem cells and/or progenitor cells.

Also, the invention provides the use of an agent capable of up-regulating the expression level of a catecholamine receptor in hematopoietic stem cells or progenitors, except of a myeloid cytokine, in the manufacture of a medicament for improving or facilitating hematopoietic stem cell transplantation (SCT) and/or progenitor cell transplantation therapy for repopulation of mature blood cell lineages.

In one embodiment of the invention, the agent capable of up-regulating expression level of the catecholamine receptor is an expression vector encoding said neurotransmitter catecholamine receptor or a vector capable of inducing the expression level of the endogenous catecholamine receptor.

In one aspect, the invention provides the use of a population of cells comprising hematopoietic stem cells and/or progenitors stimulated with a catecholamine receptor agonist, optionally in combination with an agent capable of up-regulating the expression level of the catecholamine receptor in stem cells or progenitors, in the manufacture of a medicament for increasing production of hematopoietic cells.

In one embodiment of the invention, the stimulated cells are collected from an individual to which the catecholamine receptor agonist, optionally in combination with an agent capable of up-regulating the expression level of the catecholamine receptor has been administered in vivo.

In another embodiment of the invention stimulation of the cells is carried out ex-vivo.

In a further embodiment of the invention, the cells are stimulated with an agent capable of up-regulating the expression level of the catecholamine receptor in stem cells or progenitors such as the myeloid cytokine GM-CSF and/or G-CSF.

In a further embodiment of the invention, the stem cells or progenitors are from a G-CSF treated donor.

The invention also relates to the use of a cell population comprising hematopoietic stem cells and/or progenitors collected from the blood of an individual administered with a catecholamine receptor agonist, optionally in combination with a myeloid cytokine, in the manufacture of a medicament for hematopoietic stem cell transplantation (HSCT) or progenitor cell transplantation therapy.

In addition, the invention relates to the use of a cell population comprising hematopoietic stem cells and/or progenitors stimulated ex-vivo with GM-CSF and/or G-CSF and a catecholamine receptor agonist in the manufacture of a medicament for improving or facilitating hematopoietic stem cell transplantation (HSCT) or hematopoietic progenitor cell transplantation therapy for repopulation of mature blood cell lineages.

Also, the invention relates to the use of a cell population comprising stem cells and/or progenitors ex-vivo stimulated with a catecholamine receptor agonist and an agent capable of up-regulating the expression level of the catecholamine receptor in stem cells and/or progenitors in the manufacture of a medicament for transplantation therapy, tissue regeneration and/or somatic cell therapy.

In one embodiment of the invention, the stem cell and/or progenitors harbor recombinant DNA.

In a further embodiment of the invention, the stem cell and/or progenitors are CD34+ stem cells and/or progenitors.

In another further embodiment of the invention, the medicament is for somatic cell therapy.

In another further embodiment of the invention, the medicament is for the therapy of a disease disorder or condition selected from cancers selected from Acute Lymphocytic leukemia (ALL), Acute Myelogenous leukemia (AML), Chronic Myelocytic leukemia (CML), Myelodysplastic syndrome (MDS), Liposarcoma, Neuroblastoma, Non-Hodgkin's lymphoma, Yolk Sac sarcoma; Blood Disorders selected from Amegakaryocytic thrombocytopenia (AMT), Aplastic anemia, Diamond-Blackfan anemia, Congenital cytopenia, Evan's syndrome, Fanconi's anemia, Kostmann's syndrome, Sickle cell anemia, Thalassemia; Inherited Metabolic Disorders such as Adrenoleukodystrophy, Bare-lymphocyte syndrome, Dyskeratosis congenital, Familial erythrophagocytic lymphohistiocytosis, Gaucher disease, Gunter disease, Hunter syndrome, Hurler syndrome, Inherited neuronal ceroid lipofuscinosis, Krabbe disease, Lanegerhans'-cell histiocytosis, Lesch-Nyhan Disease, Leukocyte adhesion deficiency, Osteopetrosis; Immunodeficiencies selected from Adenosine deaminase deficiency (ADA or SCID-ADA), severe combined immunodeficiency (SCID), Wiskott-Aldrich syndrome, X-Linked lymphoproliferative disease (XLP), Hyper-IgM immunodeficiency (HIM); neurological diseases selected from Alzheimer's, Parkinson's Disease, ALS, (also commonly known as Lou Gehrig's disease); muscular dystrophy; multiple sclerosis; arthritis; spinal cord injuries; brain injury; stroke; heart disease; liver and retinal disease; diabetes; and side effects of chemotherapy or radiation therapy.

In certain embodiments of the invention, the catecholamine receptor agonist is dopamine or a dopamine receptor agonist such as SKF81297, fenoldopam, pramipexole, ropinirole, apomorphine, bromocriptine, pergolide, cabergoline, 7-OH-DPAT, lisuride and fenoldopam.

In certain embodiments of the invention, the catecholamine receptor agonist is an adrenergic agonist, such as a beta adrenergic agonist, for example, epinephrine or norepinephrine.

In another aspect, the invention relates to the use of an antagonist of a catecholamine receptor in the manufacture of a medicament for decreasing growth, development, engraftment and/or repopulation capacity of a stem cell and/or progenitor population, wherein the stem cell or progenitor population has abnormal characteristics.

In one embodiment of the invention, the medicament is for the therapy of leukemia, such as acute myelogenous leukemia.

In a further embodiment of the invention, the antagonist is a dopamine receptor antagonist, for example, clozapine, flupenthixole, pimozide, remoxipride, lupenthixol, domperidone, chlorpromazine, haloperidol, ziprasidone, loxapine, thioridazine, metoclopramide, chlorprothixene, and droperidol.

In a further embodiment of the invention, the antagonist is an adrenergic receptor antagonist.

In another aspect, the invention provides a cell population comprising stem cells and/or progenitors suitable for transplantation therapy comprising stem cells and/or progenitors stimulated ex-vivo with a composition comprising a catecholamine receptor agonist, optionally in combination with an agent capable of up-regulating the expression level of the catecholamine receptor in the stem cells or progenitors.

In one embodiment of the invention, the cell population comprises stem cells and/or progenitors stimulated with an agent capable of up-regulating the expression level of the catecholamine receptor in stem cells or progenitors In a further embodiment of the invention, the catecholamine is dopamine or the agonist is a dopamine receptor agonist such as SKF81297, fenoldopam, pramipexole, ropinirole, apomorphine, bromocriptine, pergolide, cabergoline, 7-OH-DPAT, lisuride and fenoldopam.

In another further embodiment of the invention, the catecholamine is norepinephrine, epinephrine or the agonist is an adrenergic receptor agonist like a beta adrenergic receptor agonist.

In another aspect the invention relates to a pharmaceutical composition comprising a catecholamine receptor agonist and G-CSF and/or GM-CSF and a pharmaceutically acceptable carrier.

In another further aspect the invention relates to a pharmaceutical composition comprising dopamine or a dopamine receptor agonist and G-CSF and/or GM-CSF and a pharmaceutically acceptable carrier.

In still another aspect the invention relates to a pharmaceutical composition comprising an adrenergic receptor agonist and G-CSF and/or GM-CSF and a pharmaceutically acceptable carrier.

In still another aspect the invention relates to a pharmaceutical composition comprising norepinephrine or epinephrine and G-CSF and/or GM-CSF and a pharmaceutically acceptable carrier.

In still another aspect the invention relates to a pharmaceutical composition comprising a pharmaceutically acceptable carrier and a population of cells comprising hematopoietic stem cells and/or progenitors stimulated with a composition comprising a catecholamine receptor agonist, optionally in combination with an agent capable of inducing up-regulation of the expression level of the catecholamine receptor in stem cells or progenitors.

In one embodiment of the invention, the hematopoietic stem cells and/or progenitors are from a G-CSF treated individual.

In one embodiment of the invention, the pharmaceutical composition comprises hematopoietic stem cells and/or progenitors stimulated with an agent capable of inducing up-regulation of the expression level of the catecholamine receptor in stem cells or progenitor cells, such as a myeloid cytokine like G-CSF and/or GM-CSF.

The present invention provides a pharmaceutical composition comprising a pharmaceutically acceptable carrier and a population of cells comprising hematopoietic stem cells and/or progenitors stimulated with a catecholamine receptor agonist and G-CSF or GM-CSF.

In one embodiment of the invention, the stem cells are stimulated with G-CSF or GM-CSF in vivo.

In one embodiment of the invention, the stem cells are stimulated with G-CSF or GM-CSF in vitro.

In one embodiment of the invention, the stem cells are stimulated with the catecholamine receptor agonist in vivo.

In one embodiment of the invention, the stem cells are stimulated with the catecholamine receptor agonist in vitro.

The present invention also provides a pharmaceutical composition comprising a pharmaceutically acceptable carrier and stem cells and/or progenitor cells stimulated in vivo with a catecholamine receptor agonist, optionally in combination with a myeloid cytokine.

In addition, the present invention provides a pharmaceutical composition comprising a pharmaceutically acceptable carrier and stem cells and/or progenitor cells stimulated ex-vivo with a catecholamine receptor agonist, optionally in combination with an agent capable of up-regulating the expression level of the catecholamine receptor in stem cells or progenitors.

In one embodiment of the invention, the stem cells and/or progenitors harbor recombinant DNA.

In one embodiment of the invention, the catecholamine receptor agonist is a dopamine receptor agonist, for example, SKF81297, fenoldopam, pramipexole, ropinirole, apomorphine, bromocriptine, pergolide, cabergoline, 7-OH-DPAT, lisuride and fenoldopam.

In one embodiment of the invention, the catecholamine receptor agonist is an adrenergic agonist, such as a beta adrenergic agonist like epinephrine and norepinephrine.

The invention also relates to a method for preparing an improved or superior cell composition for use in stem cell transplantation (SCT) and/or progenitor cell transplantation, which comprises providing a population of cells comprising hematopoietic stem cells and/or progenitors and stimulating the population of cells with an agent capable of up-regulating a catecholamine receptor in stem cells or progenitors and with a catecholamine receptor agonist.

Also, the invention relates to a method for increasing migration, engraftment, repopulation capacity and/or proliferation of hematopoietic stem cells and/or progenitors in a population of cells, comprising stimulating the cell population with a catecholamine receptor agonist, optionally in combination with an agent capable of up-regulating the catecholamine receptor in the stem cells or progenitors.

In one embodiment of the invention, the stem cells and/or progenitors in the population are from a G-CSF or GM-CSF treated donor.

In one embodiment of the invention, the method includes stimulating the cells with an agent capable of up-regulating the catecholamine receptor in the stem cells or progenitor cells, such as the myeloid cytokine G-CSF and/or GM-CSF.

In addition, the invention relates to a method for preparing an improved or superior cell composition for use in stem cell transplantation (SCT) and/or progenitor cell transplantation, which comprises stimulating a population of cells comprising hematopoietic stem cells and/or progenitors with a composition comprising a catecholamine receptor agonist and with G-CSF and/or GM-CSF.

In one embodiment of the invention, stimulation with a composition comprising the catecholamine receptor agonist and with G-CSF and/or GM-CSF is carried out ex vivo.

In another embodiment of the invention, stimulation with a composition comprising the catecholamine receptor agonist is carried out ex vivo and stimulation with G-CSF and/or GM-CSF is carried out in vivo.

In another further embodiment of the invention, the stem cells and/or progenitors are stem cells comprising recombinant DNA.

The invention provides a method for preparing long-term culture initiating cells for clinical transplantation comprising providing a population of cells comprising hematopoietic stem cells, up-regulating a expression level of a catecholamine neurotransmitter receptor in the stem cells and exposing the cells to a catecholamine receptor agonist.

In one embodiment of the invention, the stem cells are from a G-CSF or GM-CSF treated donor.

In one embodiment of the invention, up-regulation of the expression level of the catecholamine receptor in the cells is carried out by exposing the cells to a myeloid cytokine such as GM-CSF and/or G-CSF.

The invention also provides a method for preparing an improved or superior hematopoietic stem cell and/or progenitor composition for use in transplantation comprising providing stem cells and/or progenitors, stimulating the cells with an agent capable of up-regulating the expression level of a catecholamine receptor in the cells and sorting cells expressing increased levels of the receptor in the surface.

In one embodiment of the invention, the cells are CD34+ cells.

In a further embodiment of the invention, the cells are CD34+/CD38−/low cells.

In a further embodiment of the invention, the agent capable of up-regulating the expression level of the catecholamine receptor is GM-CSF or G-CSF.

In another further embodiment of the invention, the agent capable of up-regulating the expression levels of the catecholamine neurotransmitter receptor is an expression vector encoding the catecholamine neurotransmitter receptor or a vector capable of up-regulating endogenous receptor expression level.

In another further embodiment of the invention, the sorted cells exhibit 2-4 folds higher level of catecholamine neurotransmitter receptor in the cell surface as compared to the level of the receptor in non-stimulated cells.

The invention provides a method for preparing long-term culture initiating cells for clinical transplantation comprising providing a population of cells comprising hematopoietic stem cells, stimulating the population of cells with GM-CSF and/or G-CSF for inducing up-regulation of the level of expression of a catecholamine receptor in the stem cells, and contacting the population of cells with the catecholamine receptor agonist.

In one aspect, the invention provides a method for enhancing bone marrow repopulation comprising transplanting into a patient in need a therapeutically effective amount of a population of cells comprising hematopoietic stem cells stimulated with GM-CSF and/or G-CSF and with a catecholamine receptor agonist.

In another aspect, the invention provides method of improving or facilitating stem cell transplantation (SCT) and/or progenitor cell transplantation therapy comprising administering to a patient in need a therapeutically effective amount of a cell population comprising stem cells and/or progenitors stimulated with a catecholamine receptor agonist, optionally with an agent capable of up-regulating the expression level of the catecholamine receptor in stem cells or progenitors.

In one embodiment of the invention, the stem cells or progenitors are hematopoietic stem cells and/or progenitors.

In another embodiment of the invention, the stem cells and/or progenitors in the population are from a G-CSF or GM-CSF treated subject.

In another embodiment of the invention, the method comprises stimulating the cells with an agent capable of up-regulating the expression level of the catecholamine receptor in stem cells or progenitors such as a myeloid cytokine, for example, GM-CSF and/or G-CSF.

In another embodiment of the invention, the stimulation with the catecholamine receptor agonist is carried out ex vivo.

In another embodiment of the invention, the stimulation with the myeloid cytokine is carried out in vivo.

In another embodiment of the invention, the stem cells or progenitors in the population are cells comprising recombinant DNA.

In another embodiment of the invention, the patient in need suffers of a disease disorder or condition selected from cancers selected from Acute Lymphocytic leukemia (ALL), Acute Myelogenous leukemia (AML), Chronic Myelocytic leukemia (CML), Myelodysplastic syndrome (MDS), Liposarcoma, Neuroblastoma, Non-Hodgkin's lymphoma, Yolk Sac sarcoma; Blood Disorders selected from Amegakaryocytic thrombocytopenia (AMT), Aplastic anemia, Diamond-Blackfan anemia, Congenital cytopenia, Evan's syndrome, Fanconi's anemia, Kostmann's syndrome, Sickle cell anemia, Thalassemia; Inherited Metabolic Disorders such as Adrenoleukodystrophy, Bare-lymphocyte syndrome, Dyskeratosis congenital, Familial erythrophagocytic lymphohistiocytosis, Gaucher disease, Gunter disease, Hunter syndrome, Hurler syndrome, Inherited neuronal ceroid lipofuscinosis, Krabbe disease, Lanegerhans'-cell histiocytosis, Lesch-Nyhan Disease, Leukocyte adhesion deficiency, Osteopetrosis; Immunodeficiencies selected from Adenosine deaminase deficiency (ADA or SCID-ADA), severe combined immunodeficiency (SCID), Wiskott-Aldrich syndrome, X-Linked lymphoproliferative disease (XLP), Hyper-IgM immunodeficiency (HIM); neurological diseases selected from Alzheimer's, Parkinson's Disease, ALS, (also commonly known as Lou Gehrig's disease); muscular dystrophy; multiple sclerosis; arthritis; spinal cord injuries; brain injury; stroke; heart disease; liver and retinal disease; diabetes; and side effects of chemotherapy or radiation therapy.

The invention relates to a method of stem cell transplantation (SCT) and/or progenitor transplantation therapy comprising administering to a patient in need a therapeutically effective amount of a population of cells comprising hematopoietic stem cells and/or hematopoietic progenitors stimulated with GM-CSF or G-CSF and with catecholamine receptor agonist.

In one embodiment of the invention, the stimulation with GM-CSF or G-CSF is carried out in vivo.

The invention relates to a method of improving or facilitating stem cell transplantation (SCT) and/or progenitor cell transplantation therapy comprising administering to a patient in need a therapeutically effective amount of a population of cells comprising stem cells and/or progenitors and a composition comprising a catecholamine receptor agonist, optionally with an agent capable of up-regulating the expression level of a catecholamine receptor in stem cells or progenitors.

In one embodiment of the invention, the method is for improving or facilitating hematopoietic stem cell transplantation (HSCT) or progenitor cell transplantation therapy.

In one embodiment of the invention, the method comprises administration of an agent capable of up-regulating the expression level of the catecholamine receptor in stem cells or progenitor cells such as a myeloid cytokine like GM-CSF and G-CSF.

In one embodiment of the invention, the stem cells and/or progenitor cells comprise recombinant DNA.

In one embodiment of the invention, the patient in need suffers from a disease disorder or condition selected from cancers selected from Acute Lymphocytic leukemia (ALL), Acute Myelogenous leukemia (AML), Chronic Myelocytic leukemia (CML), Myelodysplastic syndrome (MDS), Liposarcoma, Neuroblastoma, Non-Hodgkin's lymphoma, Yolk Sac sarcoma; Blood Disorders selected from Amegakaryocytic thrombocytopenia (AMT), Aplastic anemia, Diamond-Blackfan anemia, Congenital cytopenia, Evan's syndrome, Fanconi's anemia, Kostmann's syndrome, Sickle cell anemia, Thalassemia; Inherited Metabolic Disorders such as Adrenoleukodystrophy, Bare-lymphocyte syndrome, Dyskeratosis congenital, Familial erythrophagocytic lymphohistiocytosis, Gaucher disease, Gunter disease, Hunter syndrome, Hurler syndrome, Inherited neuronal ceroid lipofuscinosis, Krabbe disease, Lanegerhans'-cell histiocytosis, Lesch-Nyhan Disease, Leukocyte adhesion deficiency, Osteopetrosis; Immunodeficiencies selected from Adenosine deaminase deficiency (ADA or SCID-ADA), severe combined immunodeficiency (SCID), Wiskott-Aldrich syndrome, X-Linked lymphoproliferative disease (XLP), Hyper-IgM immunodeficiency (HIM); neurological diseases selected from Alzheimer's, Parkinson's Disease, ALS, (also commonly known as Lou Gehrig's disease); muscular dystrophy; multiple sclerosis; arthritis; spinal cord injuries; brain injury; stroke; heart disease; liver and retinal disease; diabetes; and side effects of chemotherapy or radiation therapy.

In one aspect, the invention relates to a method for improving or facilitating hematopoietic stem cell transplantation (HSCT) and/or hematopoietic progenitor cell transplantation and reconstitution of at least one lineage of blood cells comprising administering to a patient in need a therapeutically effective amount of a catecholamine receptor agonist and hematopoietic stem cells and/or progenitors.

In another aspect, the invention relates to a method for improving or facilitating stem cell transplantation (SCT) and/or progenitor transplantation therapy comprising administering to a patient in need a therapeutically effective amount of stem cells and/or progenitors and an agent capable of up-regulating the expression level of a catecholamine receptor in stem cells, except of a myeloid cytokine, optionally in combination with a catecholamine receptor agonist.

In another further aspect, the invention relates to method for tissue replacement, engraftment regeneration and/or repopulation therapy comprising transplanting into a patient in need a therapeutically effective amount of a cell population according to any one of claims 40 to 43.

In one embodiment of the invention, the tissue is hematopoietic, bone, cartilage, cardiac, or neural tissue.

In another further aspect, the invention relates to a method for increasing bone marrow mass comprising administering to a patient in need a therapeutically effective amount of a catecholamine receptor agonist.

In one embodiment of the invention, the catecholamine receptor agonist is a dopamine receptor agonist, for example, SKF81297, fenoldopam, pramipexole, ropinirole, apomorphine, bromocriptine, pergolide, cabergoline, 7-OH-DPAT, lisuride and fenoldopam.

In another further aspect, the invention relates to method for facilitating mobilization of stem cells or progenitors from the bone marrow and other tissues sites into the blood of a subject comprising administering to the subject a therapeutically effective amount of a catecholamine receptor agonist.

In one embodiment of the invention, the catecholamine receptor agonist is a dopamine receptor agonist, for example, SKF81297, fenoldopam, pramipexole, ropinirole, apomorphine, bromocriptine, pergolide, cabergoline, 7-OH-DPAT, lisuride and fenoldopam.

In one embodiment of the invention, the catecholamine receptor agonist is an adrenergic agonist.

In one embodiment of the invention, the adrenergic agonist is epinephrine or norepinephrine.

In another aspect, the invention relates to a method for decreasing engraftment, repopulation capacity and/or proliferation of a population of stem cells and/or progenitors in a patient in need wherein said stem cells and/or progenitors exhibit abnormal characteristics, the method comprising exposing the cell population to a therapeutically effective amount of an antagonist of a catecholamine neurotransmitter.

In one embodiment of the invention, said exposing is carried out ex-vivo.

In one embodiment of the invention, said exposing is carried out in-vivo.

In another further aspect, the invention relates to a method for treating leukemia comprising administering in a patient in need a therapeutically effective amount of an antagonist of a catecholamine neurotransmitter.

In one embodiment of the invention, the antagonist is a dopamine receptor antagonist, such as, clozapine, flupenthixole, pimozide, remoxipride, lupenthixol, domperidone, chlorpromazine, haloperidol, ziprasidone, loxapine, thioridazine, metoclopramide, chlorprothixene, and droperidol.

In one embodiment of the invention, the antagonist is an adrenergic receptor antagonist.

The invention provides a kit, comprising a first component comprising G-CSF or GM-CSF; a second component comprising at least one catecholamine receptor agonist; and a third component comprising instructions for the administration of the G-CSF or GM-CSF prior to the onset of administration of the at least one catecholamine receptor agonist.

The invention provides a method for enhancing proliferation and/or migration of primitive hematopoietic stem cells comprising stimulating the hematopoietic stem cells with a therapeutically effective amount of at least one catecholamine receptor agonist and at least one myeloid cytokine.

DETAILED DESCRIPTION OF THE EMBODIMENTS

Figure 1A:
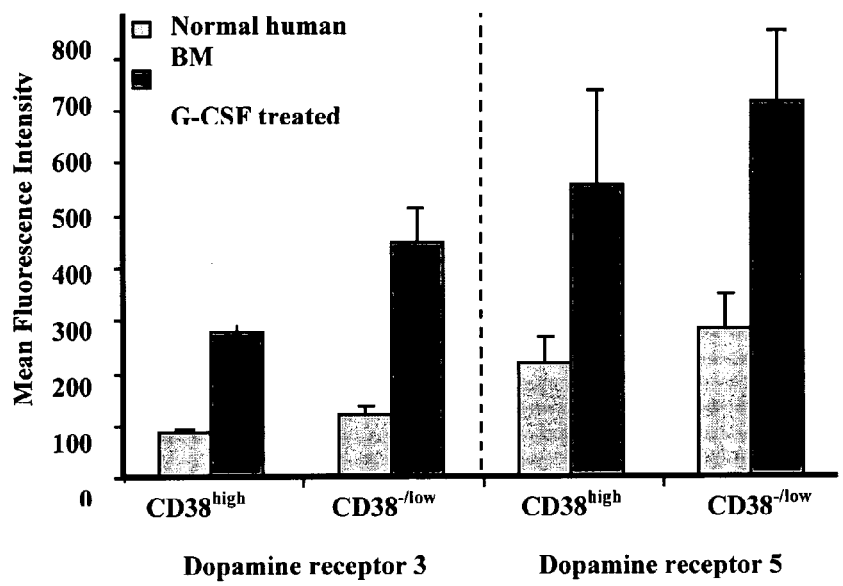
FIGS. 1A-1C show increased dopamine receptor in $CD34^+$ cells from bone marrow samples of granulocyte colony-stimulating factor (G-CSF) treated subjects. $CD34^+$ cells from bone marrow (BM) of untreated or G-CSF treated subjects were stained for dopamine 3 or dopamine 5 receptor. Cells stained with secondary antibodies (Abs) only served as control. (A) average mean fluorescence intensity from at least 3 independent experiments is shown. (B) representative flow cytometry analysis. (C) NOD/SCID chimeric mice previously engrafted with human stem cells were either untreated (Normal human BM) or treated with sub cutaneous injections of 300 µ/kg/day G-CSF for 5 days (G-CSF treated BM). Human cells recovered from the BM of the chimeric mice were indirectly immunolabeled with anti human dopamine receptor 3 or 5 antibody and with human specific anti CD34-APC CD38-PE monoclonal antibody, as indicated. Data from flow cytometry analysis is represented as percent of control in dopamine receptor mean fluorescence intensity relative to $CD34^+/CD38^{high}$ BM cells from untreated mice.

It has been found in accordance with the present invention that the activity of catecholamine receptors such as dopamine receptor, and β2 adrenergic receptor for epinephrine and norepinephrine have a central role in human hematopoietic stem cell/progenitor development, proliferation, migration, and engraftment capacity. Therefore, one aspect of the invention relates to the use of a catecholamine receptor agonist or antagonist and/or agents capable of inducing up regulation or down regulation of expression levels of the catecholamine receptor for modulating proliferation, development, migration, and/or engraftment capacity of stem cells and/or progenitors.

Dopamine receptors have been widely established as key regulators of many biological processes including cardiovascular, renal, hormonal, central nervous system and ocular functions, immune cell responses, yet their role in stem cells or hematopoiesis is currently unknown. A recent publication by Kiel et al (2005), only discloses that murine stem cells express dopamine receptor, amongst many other genes analyzed by gene array approach. Yet, this publication is silent on the role of dopamine receptors in these cells.

We show herein that a population of cells enriched with human CD34+ stem cells expresses functional dopamine 3 and dopamine 5 receptors and that a subset of more primitive cells, CD34+/CD38$^{-/low}$ cells, which are more suitable for transplantation (see below), expresses higher levels of these receptors compared to a subset of more differentiated cells, CD34+/CD38$^{high}$ cells. Furthermore, we show that: the activity of the dopamine receptor has a central role in stem cell proliferation and development since CD34$^+$ cells stimulated with dopamine receptor agonists produced increased colony-forming units (CFU-M) in agar culture (a commonly employed in vitro assay for the quantification of committed hematopoietic progenitors, see below), the activity of the dopamine receptor has a role in engraftment of stem cells since stem cells exposed to dopamine receptor agonists engraft better in the bone marrow (BM) of NOD/SCID recipient mice than non exposed cells; the activity of the dopamine receptor has a role in stem cell motility since exposure of cord blood (CB) CD34$^+$ cells to a dopamine receptor agonist induced cell polarization and spreading during adhesion to hyaluronic acid; and that dopamine receptor activity has a role in homeostasis of the number of cells in the BM under steady state conditions, since administration of dopamine receptor agonists in vivo lead to an increase in BM cellularity, while administration of dopamine receptor antagonist lead to a decrease in bone marrow cellularity and thus to a decrease in clonogenic capacity.

It has been found in accordance with the present invention that stimulating hematopoietic stem cells with an agent capable of up regulating the expression of dopamine receptors, such as GM-CSF and G-CSF, in combination with a dopamine receptor agonist increase clonogenic progenitor content and engraftment of hematopoietic stem cells. Thus, the effect of the dopamine receptor activity on stem cells may require up regulating the expression of dopamine receptors in the cells, and therefore may require the stimulation of the cells with dopamine receptor agonist in combination with an agent capable of up regulating the expression of dopamine receptors in the cells.

Our findings reveal a novel and uncharacterized phenomena since the function of dopamine receptors on human hematopoietic stem cells and progenitor cells has never been reported. We showed herein that, human hematopoietic stem and progenitor cells express dopamine receptors and respond to stimulation induced by dopamine receptor agonist/antagonist and that these receptors, traditionally investigated and known to be expressed in the neuronal system, are essential for the function of the stem cells including, but not limited to, migration, self renewal, engraftment and development.

We found according to the invention that the activity of additional receptors of catecholamine neurotransmitters such as the β2-adrenergic receptors can regulate the activity, function and expansion of hematopoietic stem cells. For example, we found that: CD34+ cells express β2-adrenergic receptor and that mobilized peripheral blood CD34+ cells express higher levels of the receptor; epinephrine and norepinephrine increase colony formation by cord blood CD34+ cells; norepinephrine has chemoattractant potential that mediates migration of cord blood mobilized peripheral blood CD34+ cells; and that norepinephrine increase engraftment of hematopoietic stem cells.

Altogether our results demonstrate a novel role of receptors of catecholamines neurotransmitters, such as dopamine receptor and β2-adrenergic receptor, in regulation, function and expansion of human stem cells/progenitors, such as hematopoietic stem cells/progenitors. Notably, our in vitro and in vivo findings reveal that catecholamine neurotransmitters directly regulate hematopoietic progenitor cell proliferation and migration which are important in transplantation therapy.

Thus, in one aspect, the invention relates to the use of a catecholamine receptor agonist for improving or facilitating stem cell transplantation (SCT) and/or progenitor cell transplantation therapy. Optionally, a catecholamine receptor agonist may be used with an agent capable of up regulating the expression of the catecholamine receptor in stem cells and/or progenitor cells. Thus, the use of a combination therapy comprising an agent capable of up regulating the catecholamine receptor and a catecholamine receptor agonist to facilitate stem cell and/or progenitor cell transplantation is also considered in the present application.

As used herein, the term "receptor agonist" is defined as a molecule that increases the activity of the receptor, for example by assisting in binding of the ligand to the receptor and/or by interacting with a receptor.

Agonist drugs activate receptors to produce the desired response. Some agonists increase the proportion of activated receptors.

Structural analogs of agonist molecules frequently have agonist properties.

A drug that acts as a partial agonist in one tissue may act as a full agonist in another.

Examples of dopamine receptor agonists include, but are not limited to, dopamine and dopamine analogs; for example SKF81297 and fenoldopam. Other examples of dopamine receptor agonist include but are not limited to pramipexole, ropinirole, 7-OH-DPAT, apomorphine, bromocriptine, pergolide, cabergoline, lisuride and fenoldopam (Wishart D S et al., 2006).

Examples of alpha adrenergic receptor agonists that can be used according to the invention include without limitation levonordefrin, epinephrine, and norepinephrine. Examples of beta adrenergic receptor agonists that can be used according to the invention include without limitation isoproterenol, metaproterenol, terbutaline Examples of agents capable of up-regulating the expression of catecholamine receptors, include but are not limited to myeloid cytokines such as GM-CSF, G-CSF and IL-3; estrogen (Lee et al., 1999); and an expression vector encoding said catecholamine receptor; and a endogenous gene activation vector (EGA) capable of inducing expression of the endogenous catecholamine receptor.

We show according to the invention that improved stem cell transplantation (SCT) and/or progenitor transplantation is achieved by using for transplantation a population of improved or superior stem cells or progenitors consisting of stem cells or progenitors stimulated with at least one catecholamine receptor agonist and/or with at least one agent capable of up regulating the expression of the catecholamine receptor. Improved stem cell transplantation (SCT) and/or progenitor transplantation may be also achieved by using for transplantation a population of cells comprising stem cells or progenitors and a composition comprising a catecholamine receptor agonist, optionally in combination with an agent capable of up regulating the expression of the catecholamine receptor.

In some transplantation procedures of the invention, stem cells and/or progenitors may be stimulated with the catecholamine receptor agonist and/or with the agent capable of up regulating the catecholamine receptor ex-vivo, prior to transplantation.

The transplanted stem cells and/or progenitors of the invention will migrate to the region of the injury where cells had died, for example bone marrow (due to side effects of chemotherapy or radiation therapy), and will differentiate into cells of the injured tissue.

The stem cells for use in the present invention are stem cells of any origin used today or to be used in the future in stem cell therapy and include, without limitation, adult stem cells, embryonic stem cells, umbilical cord blood stem cells, hematopoietic stem cells, peripheral blood stem cells, mesenchimal stem cells, multipotent stem cells, neural stem cells, stromal cells, progenitor cells, and any other type of stem cells and precursors thereof.

Stem cell transplantation therapy is similar to the process of organ transplantation, only the treatment consists of the transplantation of stem cells into the body rather than entire organs, to replace dysfunctional cells with healthy cells, thus eliminating or lessening rejection or eliminating or lessening the need for expensive and potentially dangerous immunosuppression drug therapy. Stem cell transplantation therapy is being applied to find a cure for a wide range of human diseases disorders or conditions. Stem cells have the potential of regenerating a variety of tissues, as indicated by a number of reports. Human embryonic stem cells may be used in some clinical setting. Adult stem cells might circumvent the ethical issues and safety considerations posed by embryonic stem cells. Stem cell transplantation therapy allows regeneration of tissues in many pathological conditions (as described in http://ora.ra.cwru.edu/stemcellcenter/research/research.htm). For example, stem cell transplantation therapy may be used for treating musculoskeletal, cardiovascular, hematopoietic and neurological disorders/injuries. Mesenchymal stem cells (MSC) transplantation may be used for bone and cartilage regeneration, hematopoietic stem cells (HSC) for myocardial regeneration or hematopoietic regeneration, Neural Stem Cells (NSC) for neuronal or glial replacement therapy.

Stem cells are pluripotent and have the ability to self-renew, to proliferate, and to differentiate into multiple different phenotype lineages. Embryonic stem cells, can give rise to cells derived from all three embryonic germ layers: mesoderm, endoderm, and ectoderm. Embryonic stem cells are derived from the inner cell mass of the blastocyst at a stage before it would implant in the uterine wall.

Adult stem cells are unspecialized cells found in a specialized tissue. Adult stem cells can renew themselves and become specialized to yield all of the specialized cell types of the tissue from which they originated. Adult stem cells, are capable to long-term self-renewal, namely, can make identical copies of themselves for long periods of time and can give rise to mature cell types that have characteristic morphologies and specialized functions. Since adult stem cells are scarce, it is desirable to manipulate these cells to increase their ability to proliferate in vitro so that adult stem cells can be used as a sufficient source of tissue for transplants. We have shown herein that treatment of isolated adult human hematopoietic stem and progenitor cells with dopamine receptor agonists enhance colony formation and therefore dopamine receptor agonists may be used to increase the ability of adult human hematopoietic stem cells and progenitors to proliferate or expand.

Adult stem cells for use in the present invention may be isolated from the bone marrow, peripheral blood, dental pulp, spinal cord, blood vessels, skeletal muscle, epithelia of the skin and digestive system, cornea, retina, liver, and pancreas. Adult stem cells are clonogenic. The term "clonogenic" means having the ability to generate a line of genetically identical cells, which then gives rise to the appropriate differentiated cell types. The ability of adult stem cells to generate a line of genetically identical cells, which then gives rise to the appropriate differentiated cell types can be demonstrated in vitro, for example, by using CFU-M assays, or in vivo, for example, by showing that the candidate stem cells can repopulate a particular tissue, such as the bone marrow, as shown in the examples below.

The bone marrow includes two stem cell populations, hematopoietic stem cells and stromal (or mesenchymal) cells, a mixed cell population that generates bone, cartilage, fat, fibrous connective tissue, and the reticular network that supports blood cell formation. If desired, Hematopoietic stem cells (HSCs) and bone marrow stromal cells may be separated and isolated by using a panel of specific surface markers. Another way to separate and isolate both populations of stem cells is by fractionation based on adhesion properties of the cells. For example, stromal cells adhere to a growth substrate, while hematopoietic cells do not adhere.

Hematopoietic stem cells are defined as stem cells that can maintain the continuous production of all mature blood cell lineages, while maintaining a small pool of undifferentiated stem and progenitor cells (Mayani, 2003). Three major lineages of blood cells include the lymphoid lineage, e.g. B-cells and T-cells, the myeloid lineage, e.g. monocytes, granulocytes and megakaryocytes, and the erythroid lineage, e.g. red blood cells. Certain hematopoietic stem cells are capable of differentiating to other cell types, including brain cells, and thus can be used to regenerate many different tissues (see plasticity below).

In one embodiment of the invention, the catecholamine receptor agonist is used to improve or facilitate hematopoietic stem cell transplantation (HSCT) and/or hematopoietic progenitor transplantation therapy. Sources of hematopoietic stem cells are the bone marrow, fetal liver, peripheral blood, and umbilical cord blood.

The stem cells used for the transplantation procedures of the invention may be autologous, syngeneic or allogeneic. Autologous stem cells or stem cells from HLA-matched siblings or stem cells from HLA-non-matched donors may be used for transplantation.

In one embodiment of the invention, human CD34+ from cord blood, bone marrow or MPB cells (about $1 \times 10^3$ cell/ml to $1 \times 1$-$3 \times 10^5$ cells/ml) are stimulated ex-vivo with the catecholamine receptor agonist and with the agent capable of up regulating the dopamine receptor for 2, 3 or 4 days and then transplanted.

In a further embodiment of the invention, the agent is GM-CSF (e.g. at about 5 ng/ml) and/or G-CSF (e.g. at about 100 ng/ml). In another further embodiment of the invention, the catecholamine receptor agonist is dopamine (e.g. at about 10 nM), and/or SKF (e.g. at about 1 uM) and/or 7-OH-DAPT (e.g. at about 100 nM or 1 uM) and/or norepinephrine (e.g. at about 1-10 uM and 1-10 nM), and/or epinephrine (e.g. at about 1 um and 10 nM). The concentrations of the catecholamine receptor agonists may be in the range of 0.1 nM to 10 μM, or 1 nM to 1 μM, or 1-10 μM, 100 nM to 1 μM or 1 to 10 nM. The concentrations of the GM-CSF or G-CSF can be in the range of 1 ng/ml to 500 ng/ml.

Long-term hematopoietic stem cells (HSC) or long-term replicating HSCs are cells capable of self-renewal. Whether hematopoietic stem cells are long-term replicating HSCs can be tested, for example, by transplanting human hematopoietic stem cells in a mice, let them to engraft in the mouse bone marrow creating a chimeric transplanted mouse. Then, human cells from bone marrow a chimeric transplanted mouse that can, in turn, be transplanted to another lethally irradiated mouse (secondary transplantation) and restore its hematopoietic system over some months can be defined as long-term hematopoietic stem cells (HSC) or long-term replicating HSCs. Bone marrow cells that can immediately regenerate all the different types of blood cells, but under normal circumstances cannot renew themselves over the long term are referred to as short-term progenitor or precursor cells.

The following are some of characteristics of the progenitor or precursor cells: they are relatively immature cells that are precursors to a fully differentiated cell of the same tissue type; they are capable of proliferating, but they have a limited capacity to differentiate into more than one cell type. The following progenitor cell lineages are derived from the hematopoietic stem cell: (1) the burst-forming unit-erythroid (BFU-E); (2) the colony-forming unit-granulocyte macrophage (CFU-GM); and (3) the CFU-megakaryocyte (CFU-Mk) also CFU-E, CFU-G, CFU-M, and CFU-GEMM.

Progenitor or precursor cells in fetal or adult tissues are partly differentiated cells that divide and give rise to differentiated cells. Progenitor or precursor cells are usually regarded as "committed" to differentiating along a particular cellular development pathway. Typically, a precursor or progenitor cell is an intermediate cell type of stem cells before achieving their fully differentiated state.

Stem cells in adult tissues can generate the specialized cell types of another type of tissue from which they normally reside. Thus in methods of stem cell transplantation of the present invention, stem from one tissue may be used to generate the differentiated cell types of another tissue. The term "plasticity", referred also to "unorthodox differentiation" or "transdifferentiation" means that a stem cell from one adult tissue can generate the differentiated cell types of another tissue. The differentiated cell types that result from plasticity are usually reported to have the morphological characteristics of the differentiated cells and to display their characteristic surface markers. For example, it has been reported that blood stem cells (derived from mesoderm) may be able to generate both skeletal muscle (also derived from mesoderm) and neurons (derived from ectoderm), and bone marrow stem cells (derived from mesoderm) may differentiate into another mesodermally derived tissue such as skeletal muscle, cardiac muscle or liver. Thus according to the present invention, hematopoietic stem cells stimulated with the dopamine receptor agonist, optionally in combination with an agent capable of up regulating the expression of dopamine receptors in the cells, may be used to generate skeletal muscle, neurons, cardiac muscle and liver.

Catecholamine receptors may have a function in restoring a non-hematopoietic injured tissue such as injured brain. It was found that dopaminergic activity is up regulated following traumatic brain injury (Walter et al. 2004), the ability of stem cells to leave the BM and migrate to sites of injury such as the ischemic brain (Stumm et al. 2002) requires active migratory machinery, and Nan et al (2005) recently reported that infusion of human umbilical cord blood cells ameliorates neurological deficits in rats with hemorrhagic brain injury. Thus, the catecholamine receptors expressed by migrating stem cells may participate in the regulation of cell motility, proliferation and development and relocation to sites of brain or CNS injuries, responding to signal transmitted by these systems.

Thus, in one aspect, the invention relates to a cell population, or to a group of cells, comprising stem cells and/or progenitors stimulated with a composition comprising a catecholamine receptor agonist, and optionally with an agent capable of up regulating the expression of the catecholamine receptor in stem cells or progenitors and to the use of said cell population in the manufacture of a medicament for improving or facilitating stem cell transplantation (SCT) or progenitor cell transplantation therapy for tissue regeneration, tissue repopulation and/or somatic cell therapy. When the cells are stimulated with an agent capable of up regulating the expression of a catecholamine receptor and with a catecholamine receptor agonist, they may be stimulated simultaneously with the agent and the agonist prior to transplantation, or may be first stimulated with the agent and then with the agonist. Since we have shown according to the invention that stem cells stimulated in vivo with the myeloid cytokine G-CSF exhibit higher levels of catecholamine receptors, stimulation of the cells with the agent capable of up regulating the expression of the catecholamine receptor in stem cells or progenitors can be carried out in vivo. This procedure is known as mobilization of hematopoietic cells to the blood and is typically carried out by 5 consecutive injections of G-CSF (Petit et al., 2002). Alternatively as we show in the examples below, stem cells can be stimulated ex-vivo with the agent such as a myeloid cytokine like GM-CSF or G-CSF. Before stimulation, stem cells/progenitors can be maintained in medium supplemented with heat inactivated FCS and with one or more cytokines such as Epo, SCF, IL-3 and Tpo.

Examples of disease disorder or conditions that may be treated by stem cell therapy are described in http://www.pregnancy-info.net/StemCell/treated_disease.html and include, but are not limited to, cancers such as Acute Lymphocytic leukemia (ALL), Acute Myelogenous leukemia (AML), Chronic Myelocytic leukemia (CML), Myelodysplastic syndrome (MDS), Liposarcoma, Neuroblastoma, Non-Hodgkin's lymphoma, Yolk Sac sarcoma; Blood Disorders such as Amegakaryocytic thrombocytopenia (AMT), Aplastic anemia, Diamond-Blackfan anemia, Congenital cytopenia, Evan's syndrome, Fanconi's anemia, Kostmann's syndrome, Sickle cell anemia, Thalassemia; Inherited Metabolic Disorders such as Adrenoleukodystrophy, Bare-lymphocyte syndrome, Dyskeratosis congenital, Familial erythrophagocytic lymphohistiocytosis, Gaucher disease, Gunter disease, Hunter syndrome, Hurler syndrome, Inherited neuronal ceroid lipofuscinosis, Krabbe disease, Lanegerhans'-cell histiocytosis, Lesch-Nyhan Disease, Leukocyte adhesion deficiency, Osteopetrosis; and Immunodeficiencies such as Adenosine deaminase deficiency (ADA or SCID-ADA), severe combined immunodeficiency (SCID), Wiskott-Aldrich syndrome, X-Linked lymphoproliferative disease (XLP), Hyper-IgM immunodeficiency (HIM), neurological diseases such as Alzheimer's, Parkinson's Disease, ALS, (also commonly known as Lou Gehrig's disease); muscular dystrophy; multiple sclerosis; arthritis; spinal cord injuries; brain injury; stroke; heart disease; liver and retinal disease; diabetes; and to alleviate the side effects of chemotherapy or radiation therapy such as myelosupression and peripheral blood cytopenia.

The present invention provides populations of cells comprising improved or superior stem cells or progenitors suitable for use in transplantation, tissue replacement, tissue engraftment, tissue regeneration, tissue repopulation and/or cell therapy, and methods for preparing these population of cells. The invention describes improved populations comprising stem cells and/or progenitors stimulated ex-vivo with a catecholamine receptor agonist, and optionally with an agent capable of inducing up-regulation of the catecholamine receptor expression in stem cells or progenitors.

One method for preparing an improved stem cell/progenitor composition according to the present invention comprises stimulating a population of cells comprising stem cells or progenitor cells with an agent capable of up-regulating the catecholamine receptor in the stem cells or progenitor cells of the population, ex-vivo or in vivo, and with a composition comprising a catecholamine receptor agonist ex-vivo. When stimulation of the cells with the agent is carried out in vivo, for example by injection of the agent in an individual, a population of cells comprising stem cells and/or progenitors are collected from the blood of the mammal and stimulated ex-vivo with the composition comprising the catecholamine receptor agonist. In one embodiment of the invention, the method allows obtaining an improved cell composition for use in hematopoietic stem cell transplantation (HSCT) and comprises stimulating a population of cells comprising hematopoietic stem cells or hematopoietic progenitor cells with G-CSF and/or GM-CSF in vivo and/or ex-vivo and with a composition comprising a catecholamine receptor agonist such as dopamine or and agonist thereof, epinephrine and/or norepinephrine ex-vivo.

A population of cells comprising improved or superior stem cells or progenitors suitable for transplantation may be for example, a population of cells comprising stem cells or progenitors that exhibits, when tested in the murine model shows significantly more engraftment, e.g. about 2-fold more engraftment, compared to a control population of cells; when tested in secondary transplantation model the percent of engraftment is significantly higher than in primary recipients; and/or when tested in the colony formation assay exhibits significantly more colony formation than control cells.

Long-term replicating HSCs are important for developing HSC-based cell therapies. The following set of protein markers of blood cells are associated with increased likelihood that the cell are of the long-term HSC type: CD 34$^+$, Thy1$^{+/low}$, CD38$^{low/-}$, C-kit$^{-/low}$, lin$^-$ (negative for lineage markers).

We found according to the invention that: CD34$^+$/CD38$^{-/low}$ cells express higher levels of both types of dopamine receptors compared to a subset of more differentiated cells CD34$^+$/CD38$^{high}$ cells. Thus, stimulation of a stem cell population with a composition comprising a catecholamine receptor agonist will most likely affect the CD$^{34+}$/CD38$^{-/low}$ cells in the population. Also, improved or superior cell populations for transplantation comprising stem cells and/or progenitors may be obtained by a method comprising stimulating a population of cells comprising stem cells or progenitors with an agent capable of up regulating catecholamine receptor expression and isolating or sorting cells expressing increased levels of catecholamine receptor in the surface, for example levels that are 2-4 folds higher than the levels in untreated control cells.

We found according to the invention that stem cells and/or progenitor cells such as hematopoietic stem cells and progenitors, exhibiting increased catecholamine receptors in their surface are suitable for transplantation. For example, we found that stimulation of hematopoietic stem cells and progenitors with G-CSF and GM-CSF induced high expression of dopamine receptors on the primitive CD$^{34+}$/CD38$^{-/low}$ cells. Also, in vivo stimulated (mobilized) CD34+ cells with G-CSF express higher levels of β2-adrenergic receptor. Also, inducing activity of these receptors by stimulation of mobilized hematopoietic stem cells and progenitors with epinephrine and norepinephrine resulted in increased migration and engraftment potential of hematopoietic stem cells and increase in proliferation or colony formation by hematopoietic stem cells.

Thus, in one embodiment of the invention improved or superior cell populations for transplantation comprising stem cells and/or progenitors is obtained by a method comprising: stimulating a population of cells comprising stem cells or progenitors with an agent capable of up regulating catecholamine receptor expression (in vivo or ex-vivo); sorting for cells expressing CD34$^+$/CD38$^{-/low}$; sorting for cells expressing high level of catecholamine receptors on the surface, for example for cells expressing levels of catecholamine receptors that are 2-4 folds higher than the levels of catecholamine receptors in control cells (not treated with the agent); and stimulating the cells with the catecholamine receptor agonist.

The agent may be GM-CSF or G-CSF and the stimulation may last for 2, 3, 4 or up to 5 days, or for shorter or longer times. Mobilized stem cells and/or progenitors from a GM-CSF or G-CSF treated individual may be used in the method. The cells may be sorted or isolated by methods known in the art, for example, labeling of specific markers in cells and sorting the cells by Fluorescence Activated Cell Sorter (FACS).

The hallmark of true hematopoietic stem cells is their ability to long-term reconstitute large numbers of all blood cell lineages. Considerable efforts have been devoted by many investigators in the field of transplantation and gene therapy to find conditions suitable for inducing proliferation and expansion of human stem cells in vitro. A requisite for successful stem cell expansion would be to efficiently promote proliferation of true stem cells without a concomitant loss of long-term reconstituting ability. Since we have shown herein that exposure of stem cells to dopamine receptor agonist in vitro resulted in an increase of the rate of secondary engraftment, an improved stem cells population having enhanced amount of long-term culture initiating cells (LTC-IC) may be prepared employing a method comprising stimulating a population of cells comprising stem cells with a catecholamine receptor agonist.

In one aspect, the invention relates to a method for increasing proliferation, development, migration, engraftment and/or repopulation capacity of stem cells or progenitors in a cell population. One such method comprises providing a cell population comprising stem cells or progenitors and contacting the population of cells with a catecholamine receptor agonist, and optionally, with an agent capable of up-regulating the catecholamine receptor in cells.

We found according to the invention that a population of cells comprising stem cells, which were stimulated with a catecholamine receptor agonist ex vivo maintained long-term culture initiating cells. These cells are true hematopoietic stem cells, which have the ability to long-term reconstitute large numbers of all blood cell lineages.

Thus, it is another object of the invention to provide a method for preparing long-term culture initiating cells for clinical transplantation, comprising stimulating a population of cells comprising stem cells with a catecholamine receptor agonist. The long-term culture initiating cells obtained by this method are suitable for stem cell transplantation, tissue replacement, engraftment repopulation and/or cell therapy. One of the methods of the invention for preparing long-term culture initiating cells comprises providing a population of cells comprising stem cells, up-regulating dopamine receptor expression in the stem cells and exposing the cells to a dopamine receptor agonist. In one embodiment of the invention, the method for preparing long-term culture initiating cells for clinical transplantation comprises providing a population of cells comprising hematopoietic stem cells, stimulating the population of cells with GM-CSF and/or G-CSF for inducing up-regulation of dopamine receptor expression in the stem cells, and contacting the population of cells with a catecholamine receptor agonist.

In one aspect, the invention provides methods of stem cell transplantation (SCT) therapy and/or methods for enhancing bone marrow engraftment of stem cells and/or bone marrow repopulation. One of the methods of improving or facilitating stem cell transplantation therapy (SCT) comprises administering/injecting or transplanting into a patient in need a therapeutically effective amount of stem cells stimulated with a composition comprising a catecholamine receptor agonist, and optionally with an agent capable of up regulating the expression of the catecholamine receptor in stem cells or progenitors. In one embodiment of the invention the cells are obtained from a myeloid cytokine (e.g. GM-CSF or G-CSF) treated subject and these cells are stimulated ex-vivo with a catecholamine receptor agonist. In a further embodiment of the invention, the method is for improving or facilitating hematopoietic stem cell transplantation (HSCT) and reconstitution of at least one lineage of blood cells. In another further embodiment, the method comprises administering to a patient in need a therapeutically effective amount of a population of cells comprising hematopoietic stem cells stimulated with GM-CSF or G-CSF and with a catecholamine receptor agonist receptor agonist ex-vivo. A further method comprises administering a therapeutically effective amount of stem cells that prior to administration were sorted for enhanced expression of a catecholamine receptor.

In certain embodiments of the invention the stem cells are from G-CSF treated donors. In other embodiments the stem cells are CD34+ enriched, CD34+/CD38−/low enriched and/or catecholamine receptor enriched, for example, by sorting the cells with a specific antibody to the receptor labelled. In some embodiments the invention relates to uses methods or compositions for stem cell transplantation, and particularly for hematopoietic stem cell transplantation (HSCT). In further embodiments, the invention describes uses methods or compositions for tissue regeneration and/or reconstitution therapy, such as hematopoietic, bone, cartilage, cardiac and neural tissue regeneration and/or reconstitution.

According to the invention, stimulating exposing or contacting the population of cells comprising stem cells or progenitors with the substances that were described in the invention (e.g. receptor agonist, antagonist and/or the agent that induce up-regulation of the receptor in stem cells or progenitors) may be carried out by administration of the substance in-vivo and/or ex-vivo.

In vitro genetic manipulation of hematopoietic stem cells (HSCs) opens a new field for somatic gene therapy. Somatic gene therapy is defined as delivery of genetically engineered genes to somatic cells in order to treat a disease. The ultimate goal of genetic therapy is to replace in situ a defective gene sequence. Using available vectors and HSCs as targets, somatic gene transfer typically results in ectopic expression of the transgene. Thus, the stem cells or progenitor cells according with the invention may comprise stem cells or progenitor cells harboring recombinant DNA encoding for a therapeutic polypeptide and thus expressing the therapeutic polypeptides and can be used in cell therapy such as somatic gene therapy.

For example, Cystic fibrosis (CF), the most prevalent, fatal genetic disorder in the Caucasian population, is caused by mutations of CF transmembrane conductance regulator (CFTR). A recent report (Wang et al., 2005) discloses that adults stem cells such as mesenchymal or marrow stromal stem cells (MSCs) possess the capacity of differentiating into airway epithelia and that MSCs from Cystic fibrosis (CF) patients and are amenable to CFTR gene correction.

Release and mobilization of stem cells from the bone marrow and other sites into the circulation is induced in subjects for harvesting stem cells from the blood for clinical transplantation. Currently, the method used to recruit and collect human stem cells from the circulation for transplantation to treat diseases such as lymphoma involves multiple stimulation with myeloid cytokines such as G-CSF and GM-CSF. However, some individuals fail to mobilize adequate amounts of stem cells and therefore need to be operated to harvest stem cells trough bone marrow aspirates. We have shown according to the invention that catecholamine receptor agonists increased motility of stem cells, and that catecholamines behave as chemo-attractants. Thus, injecting catecholamines agonists to the circulation may increase chemotaxis of stem cells from internal organs (e.g. bone marrow and spleen) into the circulation. Therefore, the present invention contemplates the use of catecholamine receptor agonist in the manufacture of a medicament for facilitating mobilization of stem cells into the circulation of a patient for autologous cell transplantation or into the circulation of a healthy subject for allogeneic transplantation.

Decreasing growth, development, migration, engraftment or repopulation of stem cells or progenitor populations may be desired in certain situations, for example, in diseases disorders or conditions in which the pathology or course of a disease disorder or condition involves stem cells or progenitor populations expressing abnormal characteristics such as uncontrolled growth. For example, acute myelogenous leukemia (AML) is a type of cancer characterized by the abundance of immature white blood cells, resulting from altered hematopoiesis eventually leading to decrease of white blood cells in the bone marrow and peripheral blood. Such decrease of growth, development, migration, engraftment or repopulation of stem cells or progenitor populations may be achieved using a catecholamine receptor antagonist.

As used herein, the term "receptor antagonist" is defined as a molecule that decreases the activity of the receptor, for example by disrupting or impeding binding of the ligand to the receptor, by interacting with a receptor.

Antagonists prevent receptor activation. Preventing activation has many effects. Antagonist drugs increase cellular function if they block the action of a substance that normally decreases cellular function. Antagonist drugs decrease cellular function if they block the action of a substance that normally increases cellular function.

Receptor antagonists can be classified as reversible or irreversible. Reversible antagonists readily dissociate from their receptor; irreversible antagonists form a stable, permanent or nearly permanent chemical bond with their receptor (e.g., in alkylation). Pseudo-irreversible antagonists slowly dissociate from their receptor.

In competitive antagonism, binding of the antagonist to the receptor prevents binding of the agonist to the receptor. In noncompetitive antagonism, agonist and antagonist can be bound simultaneously, but antagonist binding reduces or prevents the action of the agonist. In reversible competitive antagonism, agonist and antagonist form short-lasting bonds with the receptor, and steady state between agonist, antagonist, and receptor is reached. Such antagonism can be overcome by increasing the concentration of the agonist.

Structural analogs of agonist molecules frequently have antagonist properties; such drugs are called partial (low-efficacy) agonists, or agonist-antagonists.

Examples of dopamine receptor antagonist include, but are not limited to, clozapine, flupenthixole, pimozide, remoxipride, lupenthixol, domperidone, chlorpromazine, haloperidol, ziprasidone, loxapine, thioridazine, metoclopramide, chlorprothixene, and droperidol (Wishart D S et al., 2006).

Examples of adrenergic receptor antagonists that can be used in the practice of the invention include without limitation phentolamine, phentolamine hydrochloride, mesylate, tolazoline, yohimbine, rauwolscine, doxazosine, prazosine, tetrazosine and trimazosine and beta blockers such as labetolol, atenolol, metoprolol, betaxolol, bisoprolol, nadolol, pindolol, maprotiline, and bretylium.

The present invention provides also pharmaceutical compositions including cells or molecules or agents according to the invention and a pharmaceutically acceptable carrier. For example, pharmaceutical compositions may comprise stem cells and/or progenitors and/or a catecholamine receptor agonist and/or an agent capable of inducing the receptor according to the invention and a pharmaceutically acceptable carrier. In one embodiment of the invention, the pharmaceutical composition comprises a catecholamine receptor agonist, an agent capable of inducing up-regulation of catecholamine receptor in stem cells or progenitors, and a pharmaceutically acceptable carrier. In a further embodiment, the pharmaceutical composition comprises a catecholamine receptor agonist, G-CSF and/or GM-CSF and a pharmaceutically acceptable carrier.

In another further embodiment, the invention provides a pharmaceutical composition comprising a stem cell and/or progenitor cell population stimulated with a catecholamine receptor agonist, and optionally with an agent capable of inducing up-regulation of catecholamine receptor expression in stem cells or progenitors, and a pharmaceutically acceptable carrier.

In still another further embodiment, the invention provides a pharmaceutical composition comprising CD34+ hematopoietic stem cells stimulated with a catecholamine receptor agonist and with G-CSF or GM-CSF, and a pharmaceutically acceptable carrier.

The pharmaceutical composition according to the present invention includes a sufficient amount of cells, agonist/antagonist and/or agent according to the invention to achieve its intended purpose. In addition, the pharmaceutical compositions may contain suitable pharmaceutically acceptable carriers comprising excipients and auxiliaries, which facilitate processing of the active compounds into preparations which can be used pharmaceutically and which can stabilize such preparations for administration to the patient in need thereof as well known to those of skill in the art.

The cells agonist/antagonist and/or agent according to the invention might be administered to a patient in need thereof in a variety of ways. The routes of administration include intraliver, intradermal, transdermal (e.g. in slow release formulations), intramuscular, intraperitoneal, intravenous, subcutaneous, oral, epidural, topical, and intranasal routes. In addition the substance can be administered together with other components of biologically active agents such as pharmaceutically acceptable surfactants, excipients, carriers, diluents and vehicles.

We have shown herein that i.p. injection of dopamine receptor agonist is suitable for increasing cell mass in the bone marrow.

The dosage administered, as single or multiple doses, to an individual will vary depending upon a variety of factors, including the substance pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

The definition of "pharmaceutically acceptable" is meant to encompass any carrier, which does not interfere with effectiveness of the biological activity of the active ingredient and that is not toxic to the host to which it is administered. For example, for parenteral administration, the substance according to the invention may be formulated in a unit dosage form for injection in vehicles such as saline, dextrose solution, serum albumin and Ringer's solution.

A "therapeutically effective amount" is such that when administered, the said substances of the invention induces a beneficial effect in stem cell transplantation, tissue regeneration, tissue repopulation, cell therapy, and/or somatic gene therapy and/or in the treatment of tissue injury. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art.

The compounds with which the invention is concerned may be prepared for administration by any route consistent with their pharmacokinetic properties.

The active ingredient may also be administered parenterally in a sterile medium. Depending on the vehicle and concentration used, the drug can either be suspended or dissolved in the vehicle.

The term "dosage" relates to the determination and regulation of the frequency and number of doses.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

Having now described the invention, it will be more readily understood by reference to the following examples that are provided by way of illustration and are not intended to be limiting of the present invention.

EXAMPLES

The expression of catecholamine receptors on hematopoietic stem cell and their role in development and function of these cells was evaluated.

Materials & Methods (i) Human cells and reagents. Human cord blood (CB), adult G-CSF mobilized peripheral blood (MPBL) and BM from normal or G-CSF treated donors mononuclear cells were obtained after informed consent in accordance with procedures approved by the human ethics committee of the Weizmann Institute of Science. The cell surface protein CD34 is frequently used as a marker for positive selection of human hematopoietic stem/progenitor cells in research and in transplantation. $CD34^+$ cell enrichment was performed using magnetic bead separation as previously described (Spiegel A et al Blood 2004; 2900-7). Cells were cultured in RPMI 1640 medium supplemented with 10% heat-inactivated FCS, antibiotics and glutamine.

Human CB cells were obtained from full-term deliveries after informed consent. Blood samples were diluted 1:1 in PBS. Low-density MNCs were collected after standard separation on Ficoll-Paque (Pharmacia Biotech, Uppsala, Sweden) and washed in PBS. Enrichment of human $CD34^+$ cells was done with the MACS cell isolation kit and the autoMACS magnetic cell sorter (Miltenyi Biotec, Bergisch Gladbach, Germany) according to the manufacturer's instructions. Leftover mobilized peripheral blood cells, plasma and BM were obtained after informed consent from healthy donors who were undergoing mobilization for allogeneic transplantation on days 0, 5 and 6 after daily injections of G-CSF (10 μg/kg) (Filgrastim, Roche, Basel, Switzerland).

BM cells and plasma samples were also obtained from healthy donors. Twenty-four hours after one or five G-CSF injections, BM was collected by aspiration after informed consent. Human samples were used in accordance with approved procedures by the human experimentation and ethics committee of the Weizmann Institute.

In several assays the dopamine agonists (+)-1-phenyl-2,3,4,5-tetrahydro(1H)-3-benzazepine-7,8-diol hydrochloride (SKF-38393) described by Undie and Friedman (1992) as being selective for D1 receptors and 7-hydroxy-2-dipropylaminotetralin (7-OH-DPAT) (H8653) described by Levesque et al. (1992) and Damsma et al. (1993) as inducing D3 receptors; and the antagonist 2-[4-[3-[2-(trifluoromethyl)thioxanthen-9-ylidene]propyl]piperazin-1-yl]ethanol (Flupenthixol) (Sigma). Flupenthixol is a powerful antagonist of both D1 and D2 dopamine receptors for use in schizophrenia and depression, Clozapine is an antagonist of dopamine type 2 receptor for the management of severely ill schizophrenic patients who fail to respond adequately to standard drug treatment for schizophrenia. All the agents were used at the indicated concentrations.

(ii) Mice. NOD/LtSz PrKdc$^{scid}$/PrKdc$^{scid}$ (NOD/SCID) mice are bred and maintained under defined flora conditions at the Weizmann Institute in sterile micro-isolator cages. All the experiments were approved by the animal care committee of the Weizmann Institute. Eight-ten week old mice were sublethally irradiated (375 cGy, from a 60 Co source) and transplanted with human cells as indicated ($2\times10^5$ cells/mouse) 24 hours post irradiation.

(iii) Cell transplantation. Cells were injected into the tail vein of NOD/SCID in 0.5 ml of RPMI supplemented with 10% FCS.

(iv) Assessment of cell engraftment. Recipient mice were irradiated with a sublethal (350 cGy) dose from a Cesium source 24 hours prior to injection of cells. MPB or CB CD34$^+$ cells ($2$-$3\times10^5$/mouse) were treated with SKF or 7-OH-DPAT for 2-4 days and injected i.v. into NOD/SCID mice. Mice were sacrificed 5-6 weeks post transplantation of human cells for assessing human cell engraftment assessment. BM (femur, tibia and pelvis bones flushed with a syringe), spleen, and peripheral blood cells were harvested and resuspended into single cell suspensions. WBCs were counted and in some experiments MNCs were isolated from samples by standard separation on Ficol-Hypaque (Pharmacia Biotech). Human cell engraftment was assayed by flow cytometry (FACSCalibur, BD). Cells were triple-stained with CD45-FITC, CD38-PE and CD34-APC (Becton Dickinson) antibodies. Human plasma and mouse IgG were used to block Fc receptors. Human leukocytes were gated according to their expression of the pan-leukocyte marker CD45, and amongst this population the percentage of CD34$^+$/CD38$^{-/low}$ primitive cells was determined.

(v) Mobilization. Mobilization in 2- to 4-month-old BALB/c mice (Harlan, Weizmann Institute) was carried out as follows: Mice received a daily subcutaneous injection of G-CSF (Filgrastim, 300 g/kg in 250 l of 0.9% NaCl, 5% fetal calf serum (FCS) at pH 4.55) for 4 or 5 consecutive days and were killed 6 h after the last injection at the latest. Peripheral blood from mice asphyxiated with dry ice was collected by cardiac aspiration in heparinized tubes. The number of white blood cells (WBC) in the peripheral blood was determined and 20 µl of blood was seeded for the progenitor colony assay as described below. Colonies were scored 8 days after plating or latter if indicated.

Mobilization in NOD/SCID mice engrafted with human cells was performed as follows: mice received a daily subcutaneous injection of G-CSF (Filgrastim, 300 mg/kg in 250 ml 0.9% NaCl, 5% fetal calf serum (FCS), pH 4.55) for 5 consecutive days and were sacrificed 4 hrs after the last injection. Peripheral blood from mice asphyxied with dry ice was collected by cardiac aspiration in heparinized tubes. Number of WBC in the peripheral blood was determined.

(vi) Flow cytometry analysis. Phenotypes of human and murine cells were examined by immunostaining, followed by flow cytometry analysis on FACSCalibur (Becton Dickinson, San Jose, Calif.) with CellQuest software. Single cell suspension were prepared in PBS containing 0.01% sodium azide and 1% FCS. Human plasma and mouse IgG were used to block human and murine Fc-receptors. Isotype-matched control antibodies were used to exclude false positive cells. Staining was performed in 4° C. for 30 minutes. Engraftment of human cells was examined by staining with mouse anti-human CD45-Fitc, CD38-PE and CD34-APC (Becton Dickinson). Human leukocytes were gated according to their expression of the pan-leukocyte marker CD45, and amongst this population the percentage of CD34+/CD38−/low primitive cells was determined. In several experiments dopamine receptor expression on CD34+/CD38−/low was tested, cells were triple stained with mouse anti-human CD38-PE, CD34-APC and rabbit anti human dopamine receptor 3 or 5 (Calbiochem, Nottingham, UK) followed by secondary antibodies goat anti rabbit alexa 488 (Molecular Probes, Eugene, Oreg.). After staining, cells were washed in FACS buffer and analyzed by fluorescence-activated cell sorting (FACSCalibur and CellQuest software, Becton Dickinson).

(vii) Progenitor colony forming assay (CFU). In order to detect the levels of human progenitors, semisolid cultures were carried out as previously described (Peled et al. 1999). In brief, CD34$^+$ cells ($1\times10^3$ cells/ml) were plated in 0.9% methylcellulose (Sigma), 30% FCS, $5\times10^{-5}$M 2ME, 50 ng/ml SCF, 5 ng/ml IL-3, 5 ng/ml GM-CSF (R&D), and 2 u/ml Erythropoietin (Orto Bio Tech, Don Mills, Canada) together with the dopamine agonists/antagonist. In some experiments the cells were pre-incubated for 4 days with the agonists/antagonist prior to plating in the semisolid culture. The cultures were incubated at 37° C. in a humidified atmosphere containing 5% CO2 and scored 14 days later for myeloid or erythroid colonies by morphologic criteria. In experiments where the level of in vivo engraftment by primitive human cells was determined, the semisolid media contained 15% human plasma and 15% FCS.

(viii) Chemotaxis assays. Chemotaxis experiments were assayed using transwells (6.5 mm diameter, 5 µm pore; Corning Inc., Corning, N.Y.) as previously described (1). CB CD34+ cells (typically, 50,000-100,000 cells in 100 ul) with or without treatment with GM-CSF (5 ng/ml) overnight were placed in the upper chamber, and medium supplemented with ascorbic acid (Sigma) and with or without dopamine (10 nM; Sigma) was placed in the bottom chamber. Migrating cells were counted using FACSCalibur (Becton Dickinson).

(ix) Staining and histochemistry. Enriched CB CD34$^+$ cells ($1\times10^5$ to $2\times10^5$ cells per well) were plated on HA-coated cover slips for 2 hours at 37° C., either untreated or treated with SKF or 7-OH-DPAT. Samples were processed for microscopic observation as described (Goichberg et al., 2001). In brief, the adherent cells were fixed with 3% paraformaldehyde (Merck, Darmstadt, Germany) and, if indicated, permeabilized in 0.5% Triton X-100 (Sigma-Aldrich). Samples were indirectly immunolabeled at room temperature in a humidified chamber with using purified polyclonal rabbit anti human Dopamine D5 antibodies (Calbiochem, Nottingham, UK) (MCAP89; Serotec). The secondary antibodies used were Goat anti rabbit Alexa 488 conjugated (Molecular Probes, Eugene Oreg.). Phalloidin—TRITC used to detect polymerized actin, was purchased from Sigma-Aldrich. Following labeling, cells were mounted in Elvanol (Mowiol 4-88, Hoechst, Frankfurt, Germany). Immunofluorescence images were acquired using scientific-grade CCD camera and processed by the Delta Vision system using Resolve 3D software (Applied Precision, Issaquah, Wash.).

(x) Statistical Analysis. Significance levels of the data were determined by paired, two-tail Student t test analysis.

Example 1

Human Hematopoietic Stem Cells Express Dopamine Receptors on their Surface

Figure 1B:
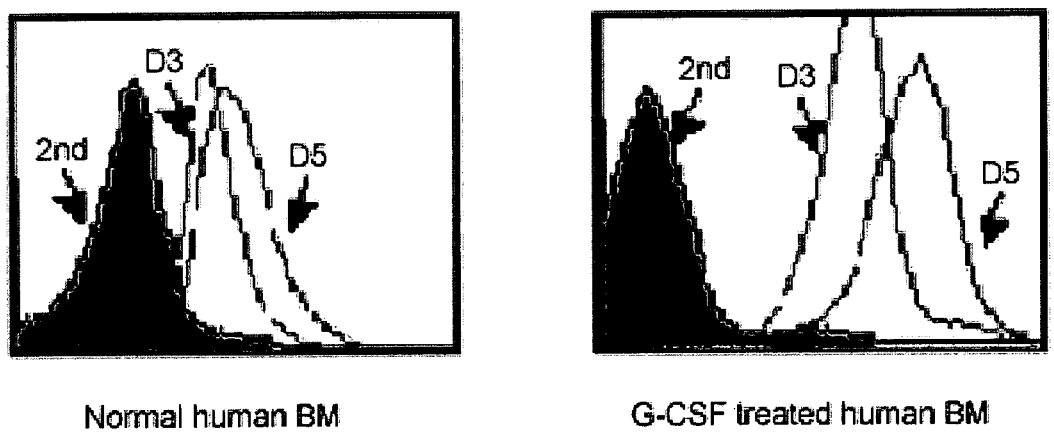

Expression of dopamine receptors type 3 and 5 was evaluated on the surface of CD34$^+$ enriched cells that were obtained from different sources. Enriched human CD34$^+$ cells were obtained, as indicated in the material and method section, from the following sources: bone marrow (BM), mobilized peripheral blood, and umbilical cord blood. We found by flow cytometry analysis that enriched human CD34$^+$ cells from all sources express both types of dopamine receptors on their surface. Interestingly, the level of expression of the receptors varied depending on the source of the cells and whether the subject was treated with G-CSF or not. For example, the expression of dopamine receptor on the surface of enriched CD34$^+$ cells derived from BM of G-CSF treated healthy donors was about 2-4 folds higher than that of enriched CD34$^+$ cells derived from bone marrow (BM) of untreated healthy human donors (FIG. 1A, B). Furthermore, we found that a more primitive subset of CD34$^+$ cells, CD34$^+$/CD38$^{-/low}$ (FIG. 2, R2), which includes a rare stem cell population more suitable for transplantation, expresses higher levels of both types of dopamine receptors compared to a subset of more differentiated cells, CD34$^+$ CD38$^{high}$ cells (FIG. 1, R1).

Example 2

Figure 1C:
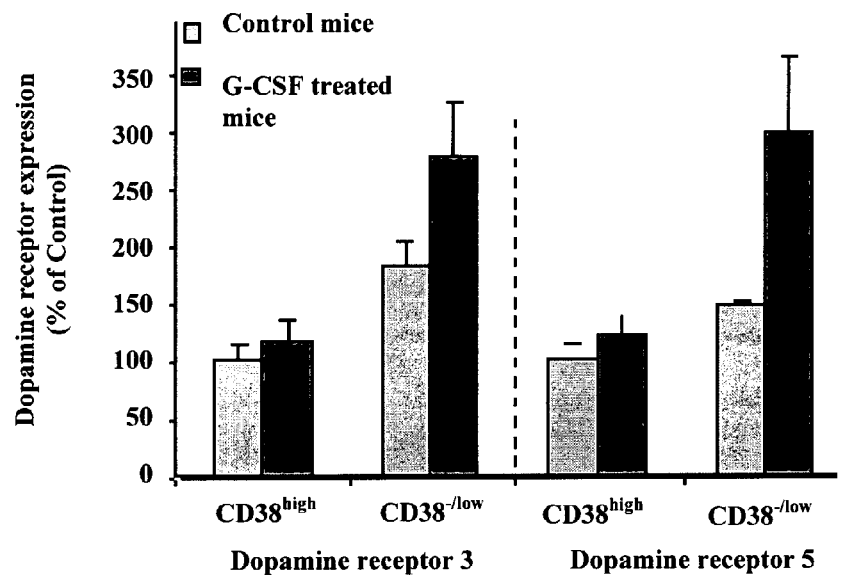
Figure 2:
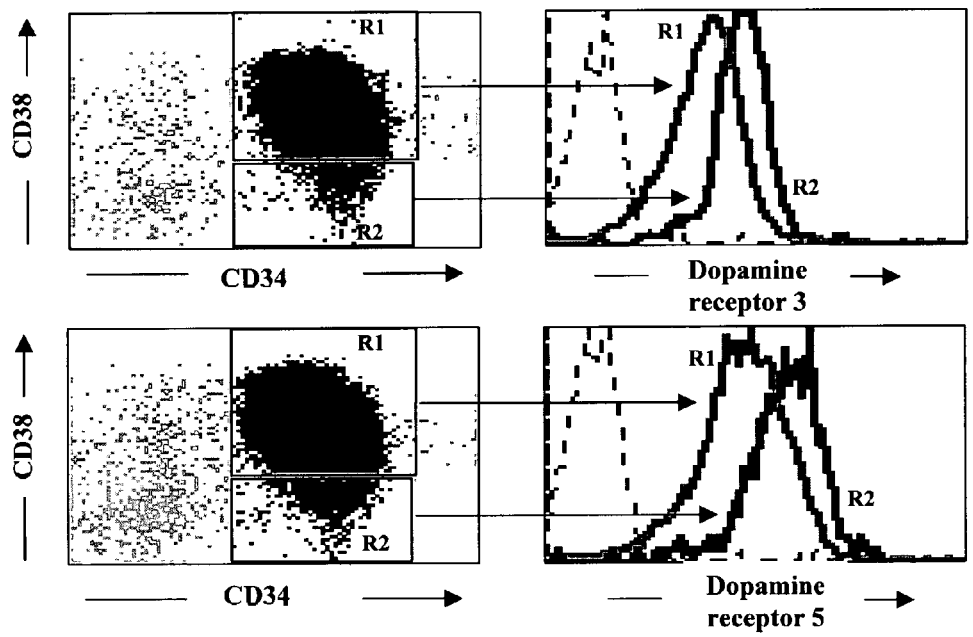
FIG. 2 shows that expression of dopamine receptors is higher in the primitive CD34+/CD38$^{-/low}$ cells than in more mature CD34+/CD38$^{high}$ cells. Human mobilized peripheral blood (MPB) CD34+ cells were stained for surface dopamine receptor 3 and 5 (upper and lower panels) and with human specific anti CD34-APC CD38-PE. The histogram plots show the levels of dopamine receptor expression in CD34+/CD38$^{high}$ (R1) and the CD34+/CD38$^{-/low}$ (R2) cell populations.
Figure 3:
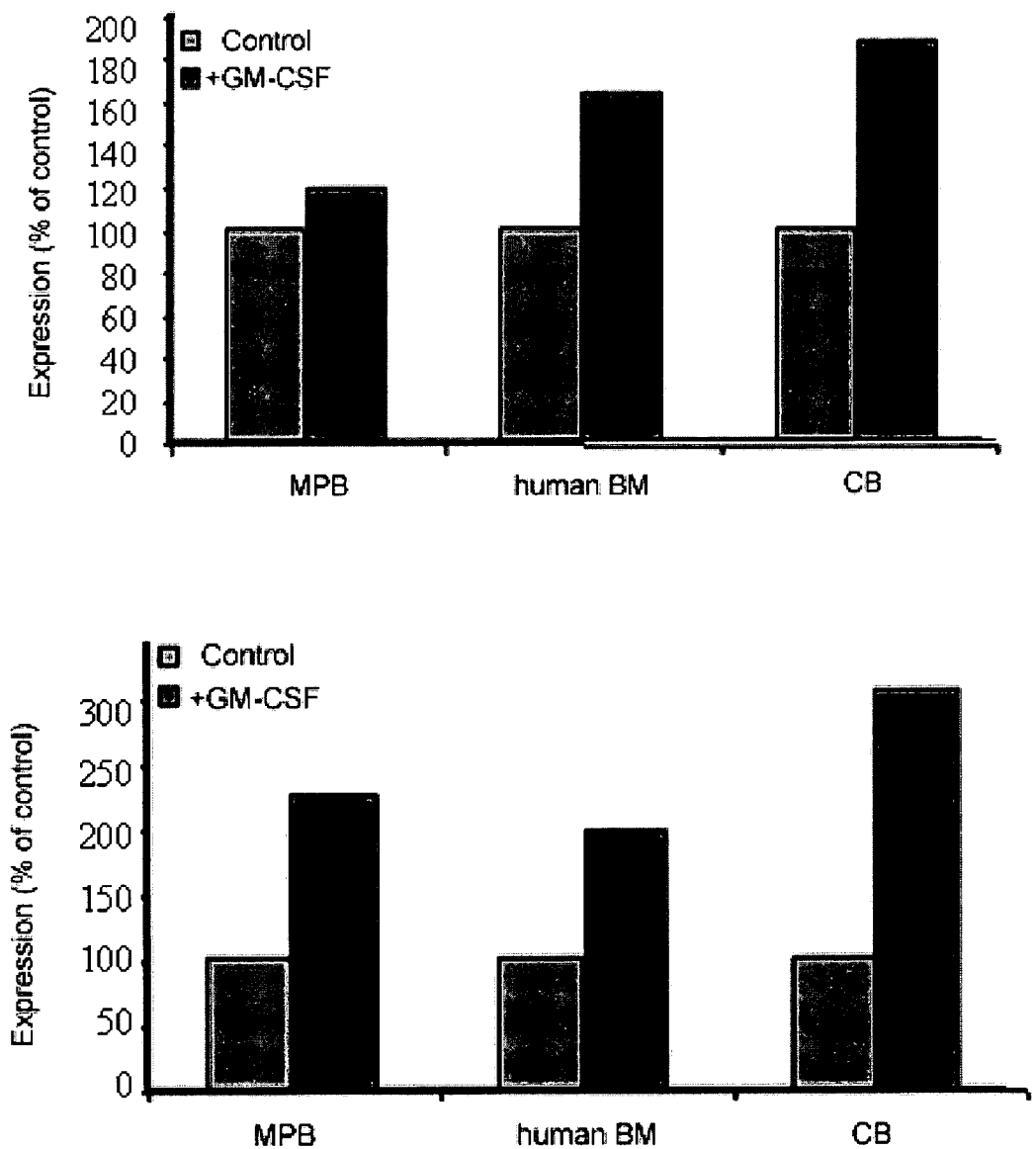
FIG. 3 shows that the level of dopamine receptor expression in CD34+/CD38$^{-/low}$ cells increases upon treatment with GM-CSF in vitro. Following a 3-day incubation with RPMI (control) or RPMI supplemented with granulocyte/macrophage-colony stimulating factor (GM-CSF), cells derived from MPB, normal human BM or cord blood (CB) were stained with human specific anti CD34-APC, CD38-PE and for dopamine receptor 5 (lower panel) or 3 (upper panel).

Myeloid Cytokines Such as G-CSF and GM-CSF Increase the Levels of Dopamine Receptor on the Surface Human CD34+ Cells In the preceding Example we showed that stem cells derived from individuals treated with G-CSF exhibited increased levels of dopamine receptors in their surface. The following experiment was carried out in a functional in vivo animal model to verify that the level of dopamine receptor in the surface of human stem cells increases upon stem cell exposure to G-CSF. This model comprises mobilization of stem cell to the peripheral blood induced by treatment of chimeric NOD/SCID mice with G-CSF. Chimeric NOD/SCID mice consist of mice that underwent xenotransplantation with human hematopoietic mononuclear cells (MNCs) from cord blood (CB). Since, as previously published Petit (2002), robust mobilization of hematopoietic stem cells to the peripheral blood (PB) is achieved after 5 daily consecutive injections of G-CSF we collected BM cells at this stage. Next, we separated MNC on Ficoll and stained the cells for Dopamine receptor 3&5 (antibody from Calbiochem), CD34 and CD38 expression [with human specific anti CD34-APC (Pharmingen) and CD38-PE monoclonal antibody (Becton dickinson), respectively], as indicated in FIG. 1C. The results obtained, as measured by flow cytometry, demonstrated that treatment of G-CSF and mobilization was accompanied by an increase in the level of dopamine receptor expression in the CD34$^+$/CD38$^{-/low}$ cell population. Thus, similarly to CD34$^+$ cells collected from human bone marrow of individuals treated with G-CSF (see preceding Example), human CD34$^+$/CD38$^{-/low}$ cells (compared to the human CD34$^+$/CD38$^{high}$) from chimeric mice treated with G-CSF exhibited increased expression of dopamine receptors on their surface (FIG. 1C). Next, the direct effect of myeloid cytokines on expression of dopamine receptor on hematopoietic stem cells was tested in vitro. For this purpose, mobilized peripheral blood, normal human bone marrow, or cord blood were incubated for 3 days with RPMI or RPMI supplemented with GM-CSF 5 ng/ml. Following this incubation, cells were triple stained with: CD34-APC(Pharmingen) CD38-PE (Becton dickinson) rabbit anti human dopamine receptor 3 Ab and rabbit anti human dopamine receptor 5 Ab (Calbiochem). Results depicted in FIG. 3 show that a 3-day incubation with GM-CSF up regulated the levels of both types of dopamine receptors, 3 and 5 in CD34$^+$/CD38$^{-/low}$ cells.

The results obtained herein show that myeloid cytokines, which induce mobilization of hematopoietic stem cells and progenitors to the peripheral blood (PB), directly increase the levels of dopamine receptor on the surface of human hematopoietic stem and progenitor cells, particularly of the more primitive population including CD34$^+$/CD38$^{-/low}$ cells.

Example 3

Figure 4A:
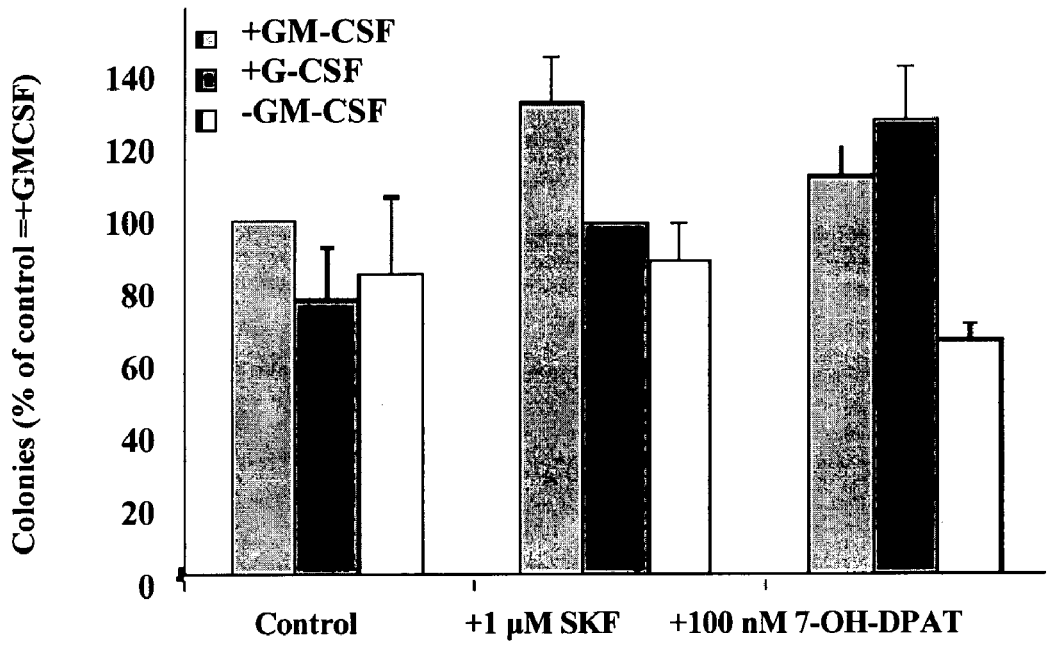
FIGS. 4A-4D show that dopamine agonists increase clonogenic progenitor content and engraftment potential of CD34+ cells. (A) CB CD34+ cells (at a concentration of $1 \times 10^3$ cells/ml) were seeded in semi solid cultures supplemented with the cytokines Erythropoietin (Epo), stem cell factor (SCF) and interleukin-3 (IL-3). GM-CSF, G-CSF, and the agonists SKF or 7-OH-DPAT were added as indicated. 14 days latter later, colonies were scored based on morphogenic criteria. The data shows the frequency of colonies in the semi solid cultures in treated cells compared to control untreated cells (treated with GM CSF but not with agonist). (B) irradiated NOD/SCID mice were injected with $1-3 \times 10^5$ MPB human CD34+ cells. Where indicated, prior to the injection CD34+ cells were incubated 2-4 days with 1 μM SKF, 100 ng/ml 7-OH-DPAT, or the dopamine antagonist clozapine. To determine engraftment of human CD34+ cells, mice were sacrificed 5 weeks post transplantation and bone marrow cells were extracted and labeled for the human marker CD45. (C) shows results of level of engraftment of CB CD34+ cells injected into irradiated NOD/SCID mice. Where indicated, cells were incubated for 2-4 days with 1 μM 7-OH-DPAT (with or without GM-CSF) prior to injection. * indicates p<0.05. (D) shows engraftment of secondary transplanted of human cells in mouse. The human cells for secondary transplantation are extracted from BM of xenotransplanted chimeric mice. The chimeric mice are produced by primary transplantation of mice with CB human cells treated with dopamine agonist or with untreated CB human cells. Thus, for secondary transplantation, irradiated NOD/SCID mice were injected with equal amounts of human CD45+ cells extracted from BM of chimeric mouse produced with human CB CD34+ cells treated with dopamine agonist 7-OH-DPAT or with human CB CD34+ untreated cells. The level of engraftment after secondary transplantation is expressed as % of engraftment from control.

Dopamine Agonists Increase Clonogenic Progenitor Content of Cord Blood CD34+ Cells GM-CSF and G-CSF are known for their role in myeloid differentiation and in stem cell regulation. It is common practice to add these cytokines to progenitor colony forming assay (CFU) in order to facilitate detection of human progenitors. In view of the role of GM-CSF and G-CSF in stem cell regulation and on our findings that these cytokines directly induce relatively high expression of dopamine receptors on the primitive CD34$^+$/CD38$^{-/low}$, we hypothesized that dopamine receptors may have a role in regulation or function of stem and progenitor hematopoietic cells. We therefore tested whether up regulation of dopamine receptor levels affects progenitor development in vitro. For this purpose cord blood CD34$^+$ cells were seeded in semi solid cultures (1×10$^3$ cells/ml in 1 ml) supplemented with the cytokines Epo (2 u/ml; Orto Bio Tech, Don Mills, Canada.), SCF (50 ng/ml; R&D) and IL-3 (5 ng/ml R&D) and with GM-CSF (5 ng/ml; R&D) or G-CSF (100 ng/ml; Roche) in order to up regulate dopamine receptor levels. To evaluate the effect of increased dopamine receptor activity, the semi solid cultures were supplemented with dopamine agonist SKF (1 µM) or 7-OH-DPAT (100 nM) or with medium as a control. As shown in FIG. 4A, SKF augmented CB CD34$^+$ CFU-C formation only in the presence of GM-CSF. Similarly the dopamine agonist 7-OH-DPAT increased colony formation in the presence of GM-CSF, but the largest increase was observed in the presence of G-CSF. No increase in colony formation was noted when the culture was not supplemented with myeloid cytokines.

These results demonstrate that the activity of the dopamine receptor has a beneficial role in stem cell regulation and differentiation.

Example 4

Figure 4B:
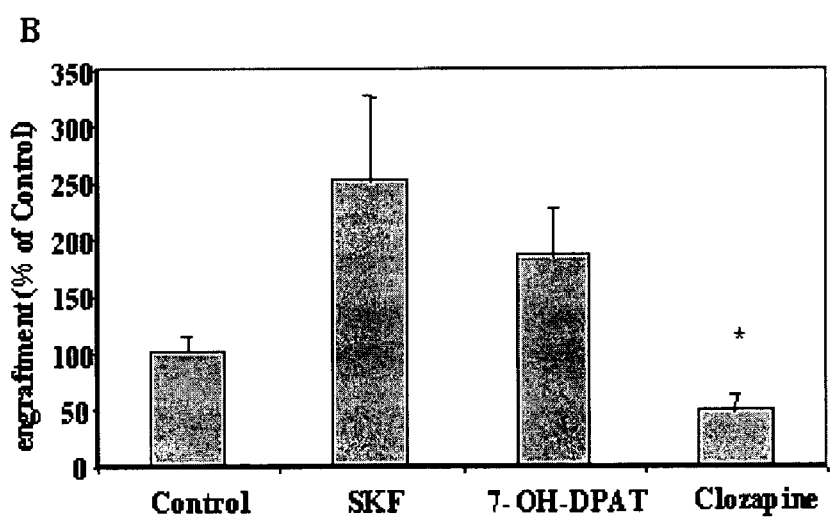
Figure 4C:
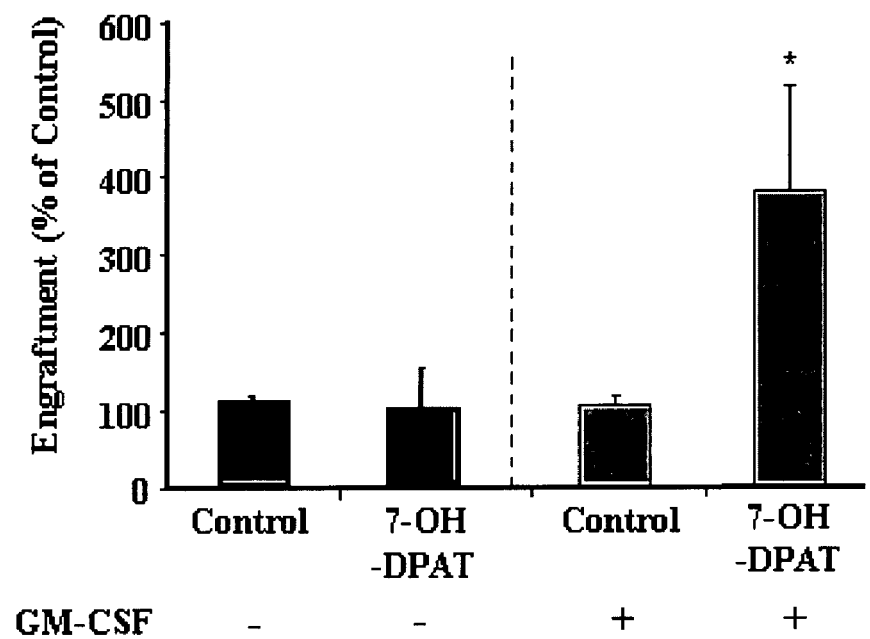

Effect of Dopamine Agonists on Engraftment of Enriched Human CD34$^+$ Cells in the Bone Marrow of NOD/SCID Mice We hypothesized that besides stem cell regulation and differentiation (as demonstrated above) dopamine receptors may have a role in stem cell functions, such as engraftment and repopulation. To assess the effect of dopamine receptor on engraftment of stem cells, mobilized peripheral blood (MPB) enriched human CD34+ cells treated ex-vivo with the dopamine agonists SKF or 7-OH-DPAT were transplanted in NOD/SCID mice and engraftment of human cell in the murine BM was determined. Briefly, 1-3×10⁵ MPB CD34+ cells were incubated for 2-4 days at 37° C. in RPMI supplemented with 10% FCS, penicillin streptomycin and L-Glutamine and treated with the dopamine receptor agonists (1 µM) SKF or (100 ng/ml) 7-OH-DPAT or were left untreated. After the incubation, the cells were injected in irradiated NOD/SCID mice. The mice were sacrificed 5 weeks post injection, BM was extracted and the BM cells were labeled for the human CD45 marker. The results are summarized in FIG. 4B and show that human stem cells treated with SKF or 7-OH-DPAT prior to injection exhibited 2-fold more engraftment in the murine BM compared to control cells. FIG. 4 C shows that the dopamine agonist only enhanced engraftment when cells were co-treated with GM-CSF and the dopamine agonist. In fact, a 50% decrease in engraftment was noted when cells were pretreated with the dopamine receptor antagonist clozapine prior to injection (FIG. 4B)

Figure 4D:
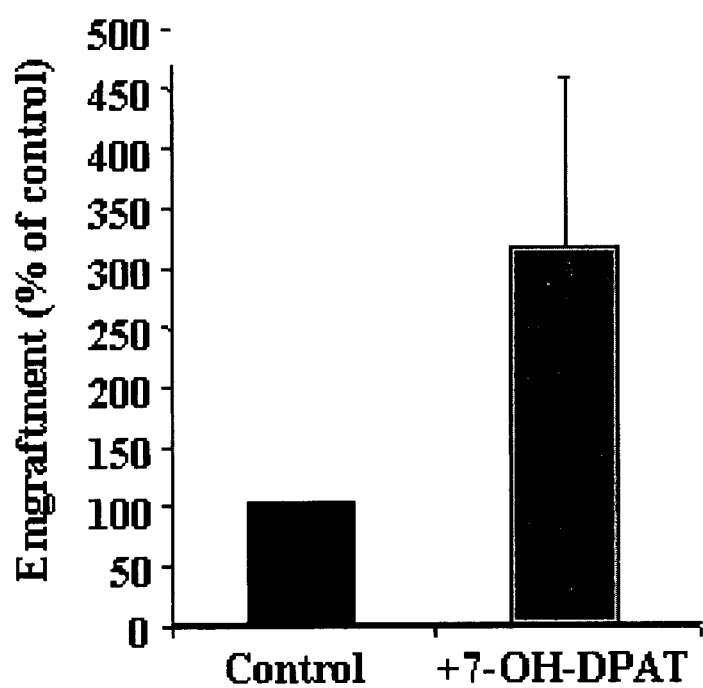

The hallmark of true hematopoietic stem cells is their ability to long-term reconstitute large numbers of all blood cell lineages. A requisite for successful stem cell expansion would be to efficiently promote proliferation of true stem cells without a concomitant loss of long-term reconstituting ability. In order to test for the effect of dopamine agonists on long-term culture initiating cells (LTC-IC), secondary transplantations were conducted. LTC-IC is a subset of the stem cell population that is more primitive and enables self renewal (Scadden D Nature 2003; 841-6). In experiments of secondary transplantation (FIG. 4D), BM cells obtained from the chimeras of the primary transplantation (and were initially injected with CD34 treated with dopamine agonist) were injected into NOD/SCID recipients. An equal amount of human cells (normalized according to the percent engraftment of the primary recipients) was injected in the secondary transplantation. In preliminary results we found that treatment with the dopamine agonists has a beneficial effect on the LTC-IC since the percent of engraftment of secondary transplanted mice is higher than in primary recipients (FIG. 4D). Thus stimulation of hematopoietic stem cells with dopamine receptor agonist induces long-term culture initiating cells as manifested by the improved capacity of secondary reconstitution.

Our results suggest that in vitro stimulation of hematopoietic stem cells or progenitors with dopamine agonists may improve the repopulation potential of this cells.

Example 5

Reduced Bone Marrow Cellularity Due to Dopamine Deprivation

Figure 5:
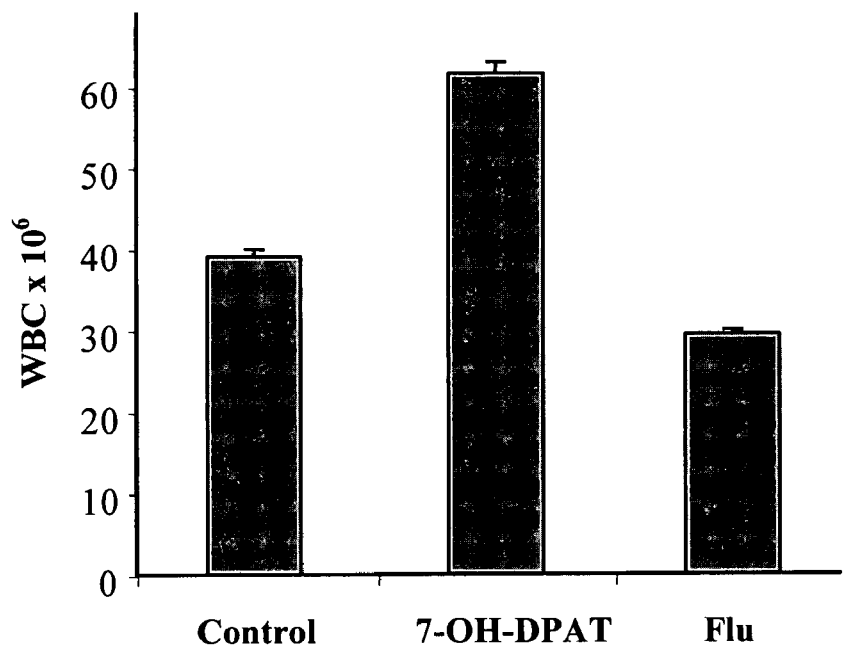
FIG. 5 shows that dopamine agonists alter BM cell mass. Mice were treated with five daily intra peritoneal injections of dopamine agonist 7-OH-DPAT (3 mg/kg), antagonist flupenthixole (Flu, 1.5 mg/kg) or remained untreated (control). The animals were sacrificed and cells were flushed from BM of control or treated mice. The results show the number of white blood counts (WBC) in 4 bones (2 femur+2 tibia in each mouse). The average of several mice is shown.

We tested whether dopamine has a role in homeostasis of the cell mass in the bone marrow. For this purpose, mice were injected with 5 daily i.p injections of the dopamine agonist 7-OH-DPAT (1.5 mg/kg) or antagonist flupenthixol 5 (3 mg/kg) or remained untreated and the bone marrow cell mass was determined. On day 5, 4 hrs after last injection, mice were sacrificed, BM cells were flushed from BM (with a syringe), and White Blood Count (WBC) was determined. We found that treatment of mice with the dopamine agonist 7-OH-DPAT lead to a 50% increase in BM cellularity, while treatment with the dopamine antagonist flupenthixol resulted in a 25% decrease in BM cellularity (FIG. 5).

Altogether, these results suggest that dopamine regulates hematopoietic proliferation in the BM.

Example 6

Figure 6A:
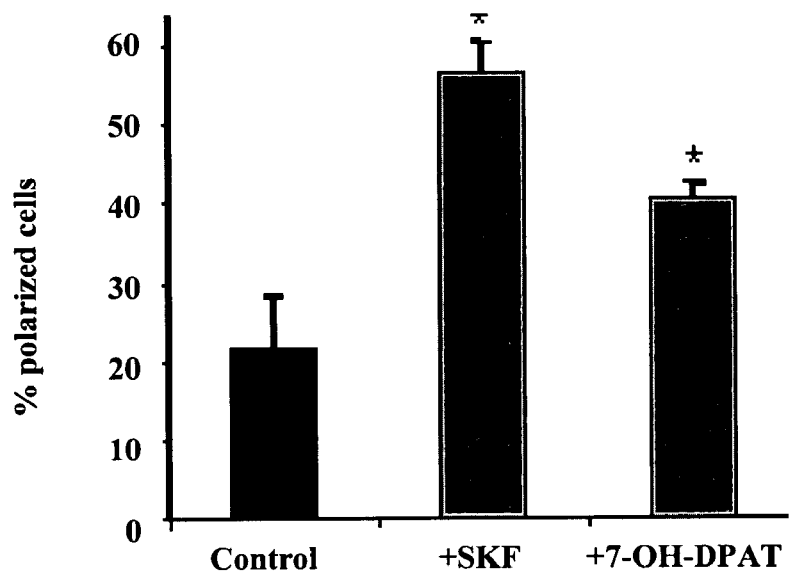
FIGS. 6A-6D show that dopamine agonists increase cell polarization of CB CD34+ cells and that dopamine has chemotactic potential. CB CD34+ cells were plated on hyaluronic acid (HA) coated cover slips either untreated (control) or in the presence of SKF or 7-OH-DPAT. After washing the cover slips the adherent cells were fixed, permeabilized and indirectly labeled with antihuman dopamine receptor 5 or with Tritc-phalloidin to detect polymerized actin. (A) shows a quantification of the number of cells with elongated and highly polarized morphology from 3 independent experiments. * indicates P<0.05 compared to control (B) shows representative pictures showing massive aggregation of dopamine receptors in polarized cells (white arrows). (C) shows results of transwell migration of human cord blood CD34+ cells (pretreated overnight with GM-CSF for 2 days) towards 10 nM dopamine placed in the lower chamber. (D) Spontaneous migration of bone marrow mononuclear cells obtained from mice treated with G-CSF and the dopamine receptor agonist SKF or 7-OH-DPAT or with G-CSF alone (Control). * indicates p<0.05.
Figure 6B:
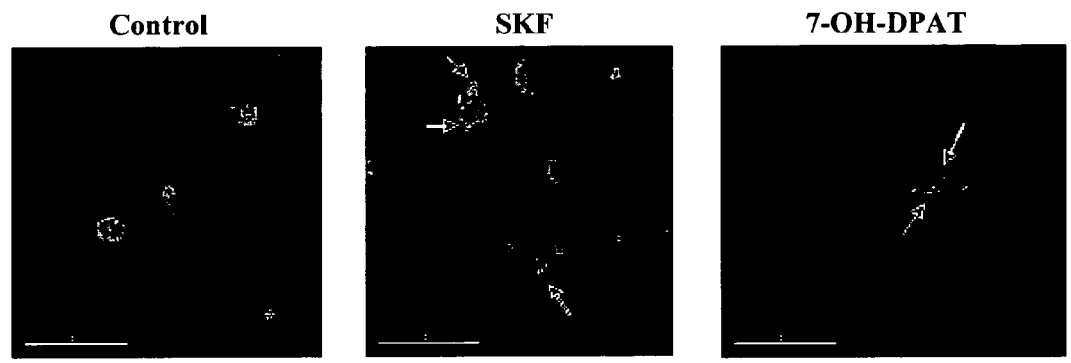

SKF and 7-OH-DPAT Induce in Cord Blood CD34+ Cells Polarization and Spreading Upon Adhesion of the Cells to Hyaluronic Acid Hyaluronic acid (HA) is an important component of the BM ECM and accounts for 40% of glycosaminoglycans produced by cultures of BM-derived stromal cells. Recent data indicate the essential role of both matrix and cell surface HA in the adhesion and migration properties of HSCs/HPCs (Avigdor et al. 2004). Development and migration of hematopoietic cells are fundamental processes that are tightly linked. Having established a role for dopamine receptors in regulation of hematopoietic stem cells (see Example 3), we next studied a possible role for the dopamine agonists in motility of CD34+ cells. Cells responding to a chemotactic stimulus display morphologic changes and cell surface receptor redistribution due to the cytoskeleton rearrangement. We assessed changes in morphology of cord blood CD34+ cells upon adhesion to hyaluronic in the presence or the absence of the dopamine agonists SFK or 7-OH-DPAT. As depicted in FIG. 6A, in the presence of the agonists SKF or 7-OH-DPAT the percent of cells that exhibited polarized morphology was more than doubled compared to control non-treated CB CD34+ cells. Many of the agonist-treated cells acquired morphologic changes manifested by enhanced spreading, cellular elongation, and multiple protrusions. We carried out immunocytochemical analysis to detect dopamine receptor 5 expressed on these cells. Interestingly, clustering of membranal dopamine receptor 5 manifested by the formation of 'dots' on the cells. Formation of strong dots indicates clustering of receptors and it was noted in polarized cells (FIG. 6B). Changes in polymerization of actin were detected in cells treated with the dopamine receptor agonists indicating cytoskeleton rearrangement in the presence of these agents.

The results obtained herein indicate that dopamine receptor has a role in migration of hematopoietic stem cells.

Figure 6C:
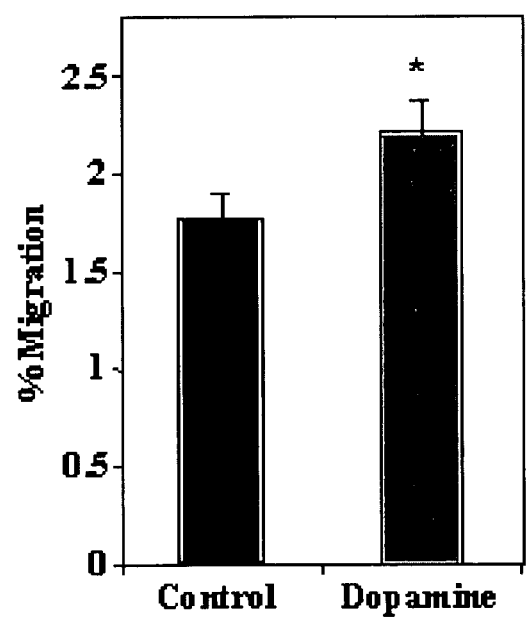
Figure 6D:
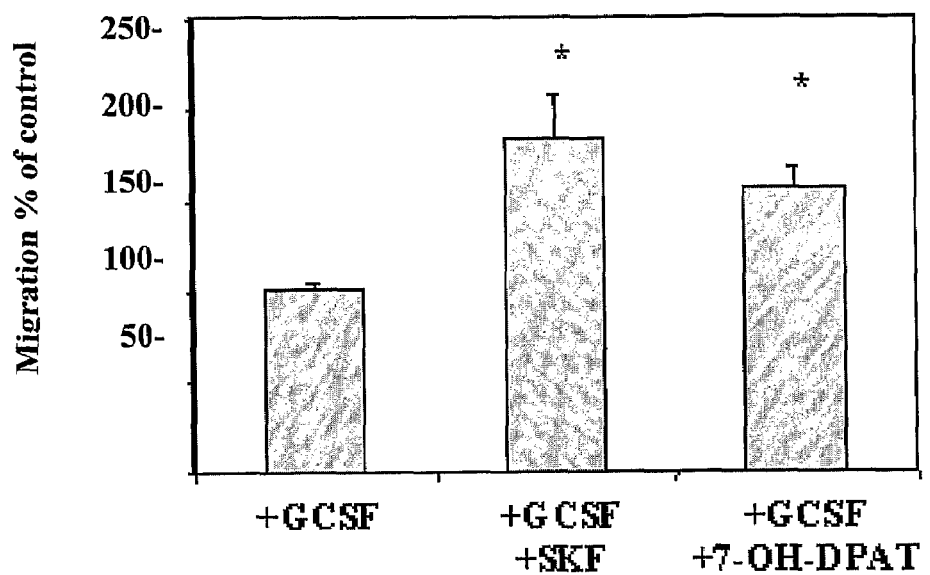

We tested the effect of dopamine (1 nM-1 uM) on in vitro migration potential of immature human CD34+ cells (50,000-100,000 cells in 100 ul). We found that dopamine placed in the lower chamber of transwells, significantly increased the migration of cord blood CD34+ enriched cells (FIG. 6C). This effect was not detected when cells were not pre-treated with the myeloid cytokine GM-CSF (data not shown). Since dopamine is highly oxidative, its agonists were used, particularly in treatments requiring longer incubation periods (FIG. 6D). Furthermore, we also show higher spontaneous migration in murine bone marrow mononuclear cells (200,00 cells in 100 ul) obtained from mice treated with G-CSF and the dopamine receptor agonists SKF or 7-OH-DPAT (the SKF or 7-OH-DPAT were injected to the mice together with the G-CSF) compared to cells obtained from mice treated with G-CSF alone (FIG. 6D).

Dopamine and dopamine agonists augmented migration of CD34+ cells, correlating with increased cell polarity.

Example 7

Figure 7A:
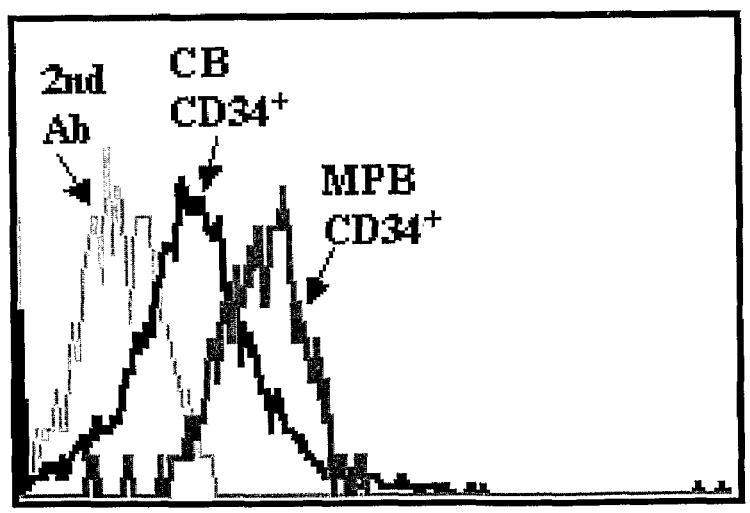
FIG. 7A-7E show that human CD34+ cells express β2adrenergic receptors and that the receptor increase colony formation, migration and engraftment of hematopoietic stem cells in response to stimulation with norepinephrine or epinephrine. (A) shows that human cord blood CD34+ cells express β2 adrenergic receptors in the surface and that and mobilized peripheral blood (MPB) CD34+ cells express higher levels of these receptors. (B) shows effect of stimulation of CD34+ cells with 1 or 10 nM norepinephrine (left panel) or 10 nM epinephrine (right panel) on colony formation in cord blood CD34+ cells (compared to control untreated cells). (C) migration of human CB CD34+ cells (pretreated overnight with GM-CSF for 1-2 days) towards 1 or 10 nM norepinephrine placed in the lower chamber of the transwell (left panel) or migration of human MPB CD34+ cells towards 10 nM norepinephrine placed in the lower chamber of the transwell (right panel). (D) Engraftment of NOD/SCID mice injected with cord blood CD34+ cells. Cells were treated for 2 days with GM-CSF with or without norepinephrine prior to injection. The number indicates the level of engraftment. (E) Engraftment of NOD/SCID mice injected with cord blood CD34+ cells. Cells were treated for 2 days with GM-CSF with or without epinephrine or norepinephrine prior to injection.

Activity of Epinephrine and Norepinephrine Receptor can Regulate Hematopoietic Stem Cell Function We carried out experiments in order to test whether CD34+ cells are regulated by additional catecholamines neurotransmitters. Employing flow cytometry analysis with beta-2 adrenergic receptor specific and labeled antibody we found that CD34+ cells express the beta-2 adrenergic receptor and that mobilized peripheral blood CD34+ cells express higher levels of these receptors (FIG. 7A).

Figure 7B:
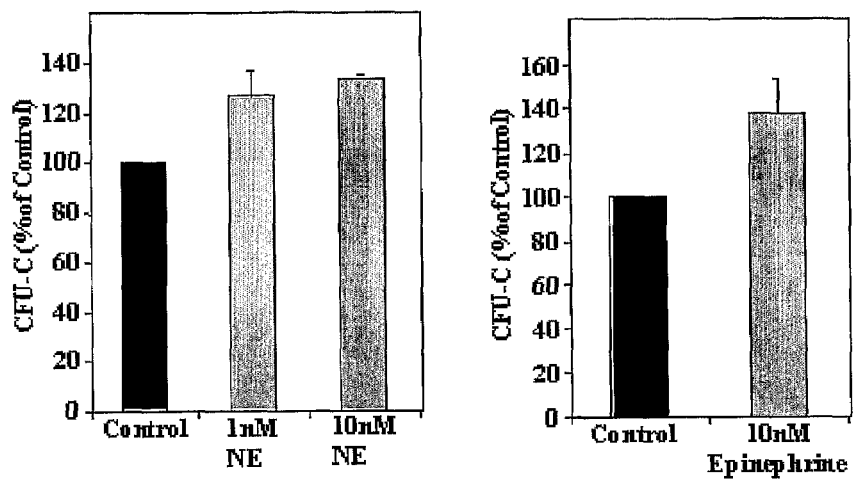
Figure 7C:
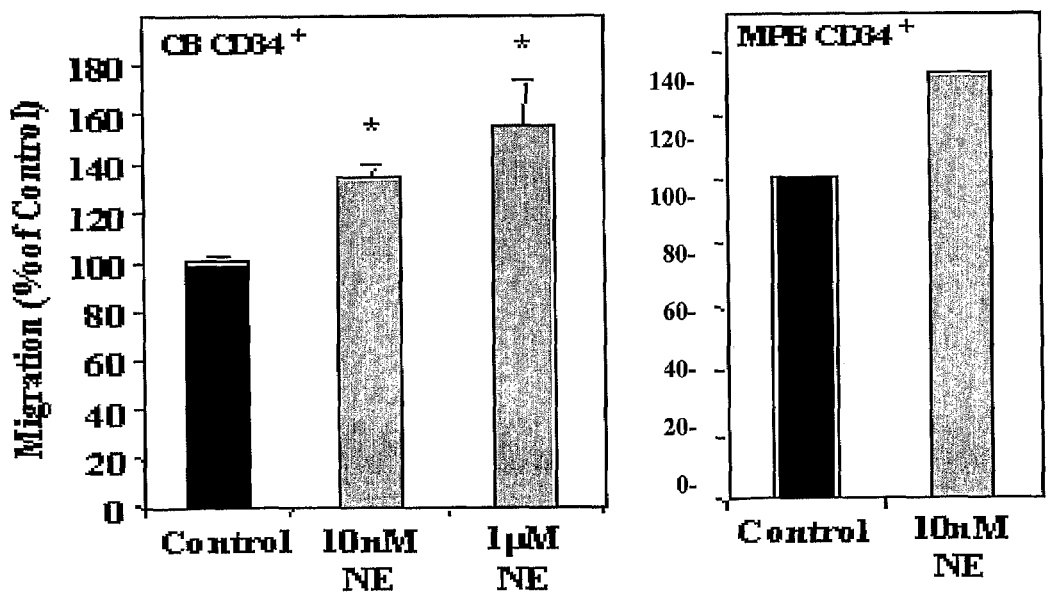
Figure 7D:
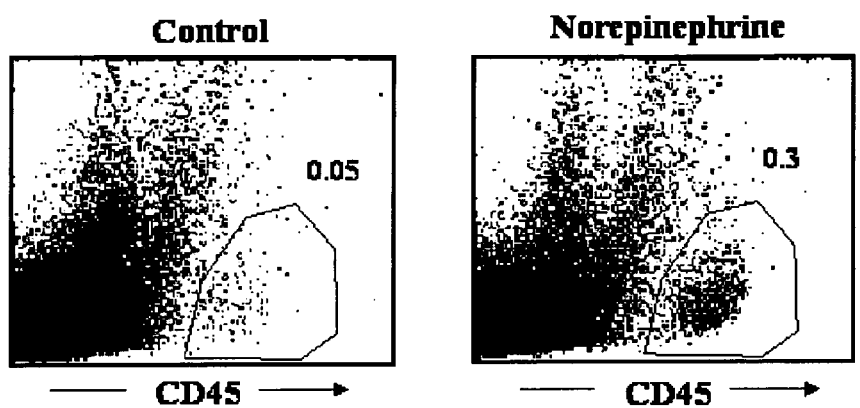
Figure 7E:
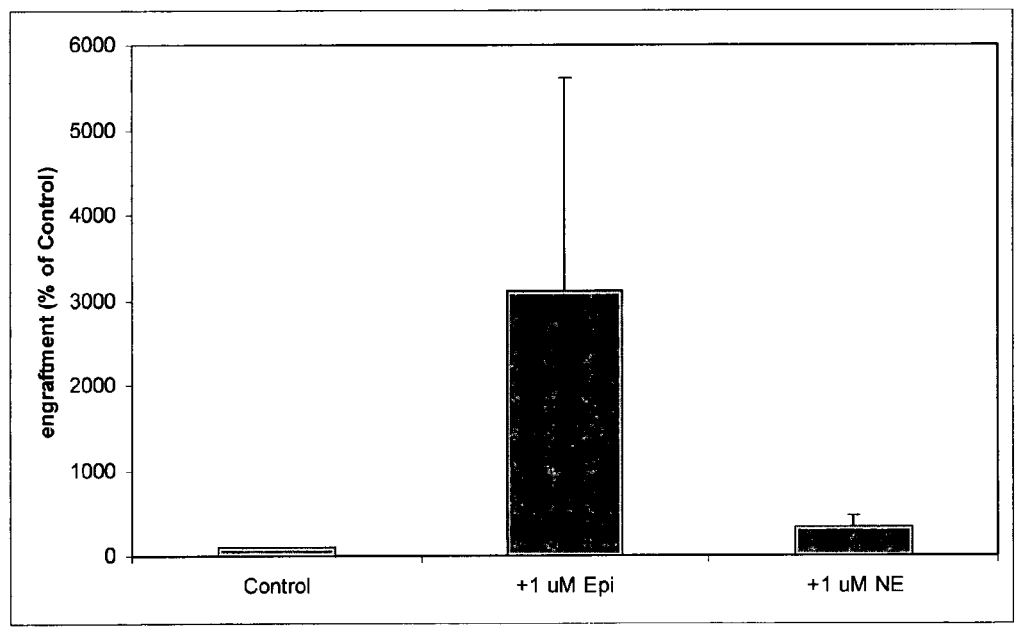

Next, the effect of the adrenergic neurotransmitters epinephrine (10 nM) and norepinephrine (1 and 10 nM) on proliferation of human CD34+ cells was assessed. The experimental conditions were similar to those conducted with the dopamine agonists. For colony assay, epinephrine and norepinephrine were added to the methyl cellulose. Both neurotransmitters were found to increase the clonogenic capacity of human cord blood CD34+ cells (FIG. 7B). For engraftment assay, cells were incubated for 2 days in RPMI supplemented with GM-CSF 5 ng/ml. Both neurotransmitters were found to increase to enhance engraftment of human CD34+ cells in NOD/SCID mice (FIG. 7D-7E).

We also found that the migration capacity of human CD34+ cells was affected by norepinephrine. For example, norepinephrine placed in the lower well increased migration of CD34+ cells indicating that migration of human hematopoietic stem and progenitor cells can be mediated by catecholamine neurotransmitters (FIG. 7C).

Our in vitro and in vivo findings reveal that catecholamine neurotransmitters directly regulate hematopoietic progenitor cell proliferation and migration.

REFERENCES

Abraham Avigdor, Polina Goichberg, Shoham Shivtiel, Ayelet Dar, Amnon Peled, Sarit Samira, Orit Kollet, Rami Hershkoviz, Ronen Alon, Izhar Hardan, Herzl Ben-Hur, David Naor, Amon Nagler, and Tsvee Lapidot "CD44 and hyaluronic acid cooperate with SDF-1 in the trafficking of human CD34+ stem/progenitor cells to bone marrow" Blood, Vol. 103, No. 8, pp. 2981-2989, (200).

Basu, S. & Dasgupta, P. S. "Dopamine, a neurotransmitter, influences the immune system". J Neuroimmunol 102, 113-24 (2000).

Besser M J, Ganor Y, Levite M. "Dopamine by itself activates either D2, D3 or D1/D5 dopaminergic receptors in normal human T-cells and triggers the selective secretion of either IL-10, TNFalpha or both" J Neuroimmunol. December; 169(1-2):161-71. (2005).

Cashman, J., Bockhold, K., Hogge, D. E., Eaves, A. C., and Eaves, C. J. "Sustained proliferation, multi-lineage differentiation and maintenance of primitive human haemopoietic cells in NOD/SCID mice transplanted with human cord blood". Br J Haematol 98, 1026-1036 (1997)

Civin, C. I., Porada, G. A., Lee, M. J., Terstappen, L., and Zanjani, E. D. "Sustained, retransplantable, multilineage engraftment of highly purified adult human bone marrow stem cells in vivo" Blood 88, 4102-4109 (1996)

Conneally E., Cashman J., Petzer A., and Eaves C. J. "Expansion in vitro of transplantable human cord blood stem cells demonstrated using a quantitative assay of their lymphomyeloid repopulating activity in nonobese diabetic-scid/scid mice" Proc. Natl. Acad. Sci. USA 94, 9836-9841 (1997)

Damsma G, Bottema T, Westerink B H, Tepper P G, Dijkstra D, Pugsley T A, Mac-Kenzie R G, Heffner T G and Wikstrom H "Pharmacological aspects of R-(+)-7-OH-DPAT, a putative dopamine D3 receptor ligand." Eur J Pharmacol 249: R9-R10 (1993)

Foley, P., Gerlach, M., Double, K. L. & Riederer, P. "Dopamine receptor agonists in the therapy of Parkinson's disease" J Neural Transm 111, 1375-446 (2004)

Goichberg P, Shtutman M, Ben-Ze'ev A, Geiger B. "Recruitment of beta-catenin to cadherin-mediated intercellular adhesions is involved in myogenic induction". J Cell Sci.; 114: 1309-1319 (2001)

Goichberg, P. et al. "cAMP-induced PKC activation increases functional CXCR4 expression on human hematopoietic progenitors" Blood. February 1; 107(3):870-9 (2006)

Goldman-Rakic, P. S., Castner, S. A., Svensson, T. H., Siever, L. J. & Williams, G. V. "Targeting the dopamine D1 receptor in schizophrenia: insights for cognitive dysfunction" Psychopharmacology (Berl) 174, 3-16 (2004).

Ilani, T., Strous, R. D. & Fuchs, S. "Dopaminergic regulation of immune cells via D3 dopamine receptor: a pathway mediated by activated T cells" Faseb J 18, 1600-2 (2004).

Kiel, M. J. et al. "SLAM Family Receptors Distinguish Hematopoietic Stem and Progenitor Cells and Reveal Endothelial Niches for Stem Cells" Cell 121, 1109-21 (2005).

Kollet O, Petit I, Kahn J, Samira S, Dar A, Peled A, Deutsch V, Gunetti M, Piacibello W, Nagler A, Lapidot T. "Human CD34(+)CXCR4 (−) sorted cells harbor intracellular CXCR4, which can be functionally expressed and provide NOD/SCID repopulation" Blood 100(8):2778-86 (2002).

Lapidot, T., Pflumio, F., Doedens, M., Murdoch, B., Williams, D. E., and Dick, J. E. "Cytokine stimulation of multilineage hematopoiesis from immature human cells engrafted in SCID mice" Science 255, 1137-1141 (1992).

Larochelle, A., Vormoor, J., Hanenberg, H., Wang, J. C. Y., Bhatia, M., Lapidot, T., Moritz, T., Murdoch, B., Xiao, X. L., Kato, I., Williams, D. A., and Dick, J. E. "Identification of primitive human hematopoietic cells capable of repopulating NOD/SCID mice using retroviral gene marking and cell purification: implications for gene therapy" Nat. Med. 2, 1329-1337. (1996).

Lee S H, Mouradian M M. R "Up-regulation of D1A dopamine receptor gene transcription by estrogen" Mol Cell Endocrinol. 156(1-2):151-7 (1999)

Lee Y, Gotoh A, Kwon H J, You M, Kohli L, Mantel C, Cooper S, Hangoc G, Miyazawa K, Ohyashiki K, Broxmeyer H E. "Enhancement of intracellular signaling associated with hematopoietic progenitor cell survival in response to SDF-1/CXCL12 in synergy with other cytokines. Blood" 99(12):4307-17. (2002)

D Levesque, J Diaz, C Pilon, M Matres, B Giros, E Souil, D Schott, J Morgat, J Schwartz and P Sokoloff "Identification, Characterization, and Localization of the Dopamine D3 Receptor in Rat Brain Using 7-[3H]hydroxy-N,N-di-n-Propyl-2-Aminotetralin" Proceedings of the National Academy of Sciences, Vol 89, 8155-8159, Copyright C by National Academy of Sciences (1992)

Levite M, Chowers Y, Ganor Y, Besser M, Hershkovits R, Cahalon L. "Dopamine interacts directly with its D3 and D2 receptors on normal human T cells, and activates betal integrin function" Eur J Immunol. (12):3504-12 (2001)

Lim, E. "A walk through the management of Parkinson s disease" Ann Acad Med Singapore 34, 188-95 (2005).

Mayani H et al. "Biology of human hematopoietic stem and progenitor cells present in circulation" Arch Med Res 34:476-488 (2003).

McCune, J. M., Namikawa, R., Kaneshima, H., Shultz, L. D., Lieberman, M., and Weissman, I. L. "The SCID-Hu mouse: Murine model for the analysis of human hematolymphoid differentiation and function" Science 241, 1632-1639. (1988)

McGrath, K. E., Koniski, A. D., Maltby, K. M., McGann, J. K., and Palis, J. "Embryonic expression and function of the chemokine SDF-1 and its receptor, CXCR4" Dev. Biol. 213:442-456 (1999).

Nagasawa, T. et al. "Defects of B-cell lymphopoiesis and bone-marrow myelopoiesis in mice lacking the CXC chemokine PBSF/SDF-1" Nature. 382:635-638 (1996).

Nan, Z., Grande, A., Sanberg, C. D., Sanberg, P. R. & Low, W. C. "Infusion of human umbilical cord blood ameliorates neurologic deficits in rats with hemorrhagic brain injury" Ann N Y Acad Sci 1049, 84-96 (2005).

Nishii K, Katayama N, Miwa H, Shikami M, Masuya M, Shiku H, Kita K. "Survival of human leukaemic B-cell precursors is supported by stromal cells and cytokines: association with the expression of bcl-2 protein" Br J Haematol. 105(3):701-10. (1999)

Peled, A. et al. "The chemokine SDF-1 stimulates integrin-mediated arrest of CD34(+) cells on vascular endothelium under shear flow" J Clin Invest 104, 1199-211 (1999).

Peled, A. et al. Dependence of human stem cell engraftment and repopulation of NOD/SCID mice on CXCR4. Science 283, 845-8 (1999).

Peled, A. et al. "The chemokine SDF-1 activates the integrins LFA-1, VLA-4, and VLA-5 on immature human CD34(+) cells: role in transendothelial/stromal migration and engraftment of NOD/SCID mice" Blood 95, 3289-3296 (2000).

Petit I, Szyper-Kravitz M, Nagler A, Lahav M, Peled A, Habler L, Ponomaryov T, Taichman R S, Arenzana-Seisdedos F, Fujii N, Sandbank J, Zipori D, Lapidot T. "G-CSF induces stem cell mobilization by decreasing bone marrow SDF-1 and up-regulating CXCR4" Nat Immunol July; 3(7):687-94 (2002) Erratum in: Nat Immunol August; 3(8): 787 (2002)

Petit, I. et al. "Atypical PKC-zeta regulates SDF-1-mediated migration and development of human CD34$^+$ progenitor cells" J Clin Invest 115, 168-76 (2005).

Sibley, D. R. & Monsma, F. J., Jr. "Molecular biology of dopamine receptors" Trends Pharmacol Sci 13, 61-9 (1992).

Spiegel A, Kollet O, Peled A, Abel L, Nagler A, Bielorai B, Rechavi G, Vormoor J, Lapidot T. "Unique SDF-1-induced activation of human precursor-B ALL cells as a result of altered CXCR4 expression and signaling" Blood. 103(8): 2900-7. (2004)

Stumm, R. K. et al. "A dual role for the SDF-1/CXCR4 chemokine receptor system in adult brain: isoform-selective regulation of SDF-1 expression modulates CXCR4-dependent neuronal plasticity and cerebral leukocyte recruitment after focal ischemia" J Neurosci 22, 5865-78 (2002).

Tavor S, Petit I, Porozov S, Goichberg P, Avigdor A, Sagiv S, Nagler A, Naparstek E, Lapidot T. "Motility, proliferation and egress to the circulation of human AML cells in transplanted NOD/SCID mice are elastase dependent" Blood. (2005)

Undie A S, Friedman E. "Selective dopaminergic mechanism of dopamine and SKF38393 stimulation of inositol phosphate formation in rat brain" Eur J Pharmacol.; 226(4): 297-302 (1992)

Vishalakumar, S., Patel, H., Moharita, A. L., Harrison, J. S. & Rameshwar, P. "The anti-proliferative effect of neurokinin-A on hematopoietic progenitor cells is partly mediated by p53 activating the 5' flanking region of neurokinin-2 receptor" Cell Signal (2005).

Walter, B. et al. "Age-dependent effects of severe traumatic brain injury on cerebral dopaminergic activity in newborn and juvenile pigs" J Neurotrauma 21, 1076-89 (2004).

Wang G, Bunnell B A, Painter R G, Quiniones B C, Tom S, Lanson N A Jr, Spees J L, Bertucci D, Peister A, Weiss D J, Valentine V G, Prockop D J, Kolls J K. "Adult stem cells from bone marrow stroma differentiate into airway epithelial cells: potential therapy for cystic fibrosis." Proc Natl Acad Sci USA. 102(1):186-91 (2005).

Wishart D S et al., DrugBank: a comprehensive resource for in silico drug discovery and exploration. Nucleic Acids Res. 1; 34 (2006).

Zanjani, E. D., Almeida-Porada, G., Livingston, A. G., Flake, A. W., and Ogawa, M. "Human bone marrow CD34– cells engraft in vivo and undergo multilineage expression that includes giving rise to CD34+ cell" Exp. Hematol. 26, 353-360 (1998).

The invention claimed is:

1. An isolated cell population comprising:
   a) CD34$^+$ hematopoietic stem cells and/or progenitors suitable for transplantation therapy stimulated ex-vivo with a composition comprising a catecholamine receptor agonist; or
   b) CD34$^+$ hematopoietic stem cells and/or progenitors suitable for transplantation therapy stimulated ex-vivo with a composition comprising a catecholamine receptor agonist in combination with an agent capable of up-regulating the expression level of the catecholamine receptor in the stem cells or progenitors.

2. The isolated cell population according to claim 1, wherein said catecholamine receptor agonist is 9-chloro-5-phenyl-2,3,4,5-tetrahydro-1H-3-benzazepine-7,8-diol (SKF81297), fenoldopam, pramipexole, ropinirole, apomorphine, bromocriptine, pergolide, cabergoline, 7-hydroxy-2-dipropylaminotetralin (7-OH-DPAT), lisuride, epinephrine or norepinephrine.

3. A pharmaceutical composition comprising a pharmaceutically acceptable carrier and a population of cells comprising:
   a) CD34$^+$ hematopoietic stem cells and/or progenitors suitable for transplantation therapy stimulated ex-vivo with a composition comprising a catecholamine receptor agonist; or
   b) CD34$^+$ hematopoietic stem cells and/or progenitors suitable for transplantation therapy stimulated ex-vivo with a composition comprising a catecholamine receptor agonist in combination with an agent capable of up-regulating the expression level of the catecholamine receptor in the stem cells or progenitors.

4. The composition according to claim 3, wherein said catecholamine receptor agonist is 9-chloro-5-phenyl-2,3,4,5-tetrahydro-1H-3-benzazepine-7,8-diol (SKF81297), fenoldopam, pramipexole, ropinirole, apomorphine, bromocriptine, pergolide, cabergoline, 7-hydroxy-2-dipropylaminotetralin (7-OH-DPAT), lisuride, epinephrine or norepinephrine.

5. A method of stem cell transplantation (SCT) and/or progenitor transplantation therapy comprising administering to a patient in need a therapeutically effective amount of a composition comprising a pharmaceutically acceptable carrier and:
   a) CD34$^+$ hematopoietic stem cells and/or progenitors suitable for transplantation therapy stimulated ex-vivo with a composition comprising a catecholamine receptor agonist; or
   b) CD34$^+$ hematopoietic stem cells and/or progenitors suitable for transplantation therapy stimulated ex-vivo with a composition comprising a catecholamine receptor agonist in combination with an agent capable of up-regulating the expression level of the catecholamine receptor in the stem cells or progenitors, said CD34+ hematopoietic stem cells and/or progenitors comprising autologous CD34+ hematopoietic stem cells and/or progenitors from said patient.

6. The method according to claim 5, wherein said patient has been treated with GM-CSF or G-CSF.

7. The method according to claim 5, wherein the stem cells and/or progenitor cells comprise recombinant DNA.

8. The method according to claim 5, wherein the patient in need suffers of a disease disorder or condition selected from:
cancers selected from Acute Lymphocytic leukemia (ALL), Acute Myelogenous leukemia (AML), Chronic Myelocytic leukemia (CML), Myelodysplastic syndrome (MDS), Liposarcoma, Neuroblastoma, Non-Hodgkin's lymphoma, or Yolk Sac sarcoma;
Blood Disorders selected from Amegakaryocytic thrombocytopenia (AMT), Aplastic anemia, Diamond-Blackfan anemia, Congenital cytopenia, Evan's syndrome, Fanconi's anemia, Kostmann's syndrome, Sickle cell anemia, or Thalassemia;
Inherited Metabolic Disorders selected from the group consisting of Adrenoleukodystrophy, Bare-lymphocyte syndrome. Dyskeratosis congenital, Familial erythrophagocytic lymphohistiocytosis, Gaucher disease, Gunter disease, Hunter syndrome, Hurler syndrome, Inherited neuronal ceroid lipofuscinosis, Krabbe disease, Lanegerhans'-cell histiocytosis, Lesch-Nyhan Disease, Leukocyte adhesion deficiency, and Osteopetrosis;
Immunodeficiencies selected from Adenosine deaminase deficiency (ADA or SCID-ADA), severe combined immunodeficiency (SCID), Wiskott-Aldrich syndrome, X-Linked lymphoproliferative disease (XLP), and Hyper-IgM immunodeficiency (HIM); or
side effects of chemotherapy or radiation therapy.

9. The method according to claim 5, wherein said catecholamine receptor agonist is 9-chloro-5-phenyl-2,3,4,5-tetrahydro-1H-3-benzazepine-7,8-diol (SKF81297), fenoldopam, pramipexole, ropinirole, apomorphine, bromocriptine, pergolide, cabergoline, 7-hydroxy-2-dipropylaminotetralin (7-OH-DPAT), lisuride, epinephrine or norepinephrine.

10. A method of stem cell transplantation (SCT) and/or progenitor cell transplantation therapy comprising administering to a patient in need an agent that up-regulates expression of the catecholamine receptor of said stem cells and/or progenitor cells in combination with a therapeutically effective amount of a composition comprising a pharmaceutically acceptable carrier and:
a) CD34+ hematopoietic stem cells and/or progenitors suitable for transplantation therapy stimulated ex-vivo with a composition comprising a catecholamine receptor agonist; or
b) CD34+ hematopoietic stem cells and/or progenitors suitable for transplantation therapy stimulated ex-vivo with a composition comprising a catecholamine receptor agonist in combination with an agent capable of up-regulating the expression level of the catecholamine receptor in the stem cells or progenitors.

11. The method according to claim 10, wherein said catecholamine receptor agonist is 9-chloro-5-phenyl-2,3,4,5-tetrahydro-1H-3-benzazepine-7,8-diol (SKF81297), fenoldopam, pramipexole, ropinirole, apomorphine, bromocriptine, pergolide, cabergoline, 7-hydroxy-2-dipropylaminotetralin (7-OH-DPAT), lisuride, epinephrine or norepinephrine.

12. A method for tissue replacement, engraftment regeneration and/or repopulation therapy comprising transplanting into a patient in need a therapeutically effective amount of a cell population comprising:
a) CD34+ hematopoietic stem cells and/or progenitors suitable for transplantation therapy stimulated ex-vivo with a composition comprising a catecholamine receptor agonist; or
b) CD34+ hematopoietic stem cells and/or progenitors suitable for transplantation therapy stimulated ex-vivo with a composition comprising a catecholamine receptor agonist in combination with an agent capable of up-regulating the expression level of the catecholamine receptor in the stem cells or progenitors.

13. The method according to claim 12, wherein said catecholamine receptor agonist is 9-chloro-5-phenyl-2,3,4,5-tetrahydro-1H-3-benzazepine-7,8-diol (SKF 81297), fenoldopam, pramipexole, ropinirole, apomorphine, bromocriptine, pergolide, cabergoline, 7-hydroxy-2-dipropylaminotetralin (7-OH-DPAT), lisuride, epinephrine or norepinephrine.

14. A method of stimulating a population of cells comprising contacting a cell population comprising hematopoietic stem cells and/or progenitors with a catecholamine receptor agonist in vitro.

15. The method according to claim 14, further comprising stimulating the cell population with an agent that up-regulates the catecholamine receptor in the stem cells or progenitors.

16. The method according to claim 15, wherein the agent is a myeloid cytokine.

17. The method according to claim 16, wherein the myeloid cytokine is G-CSF and/or GM-CSF.

18. The method according to claim 16, wherein said hematopoietic stem cells are primitive hematopoietic stem cells.

19. The method according to claim 15, further comprising sorting cells expressing increased levels of the receptor in the surface.

20. The method according to claim 14, wherein said catecholamine receptor agonist is 9-chloro-5-phenyl-2,3,4,5-tetrahydro-1H-3-benzazepine-7,8-diol (SKF 81297), fenoldopam, pramipexole, ropinirole, apomorphine, bromocriptine, pergolide, cabergoline, 7-hydroxy-2-dipropylaminotetralin (7-OH-DPAT), lisuride, epinephrine or norepinephrine.

* * * * *